United States Patent [19]

Hayashi et al.

[11] Patent Number: 5,783,703
[45] Date of Patent: Jul. 21, 1998

[54] SULFUR-CONTAINING COMPOUNDS METHOD FOR THEIR USE AND PRODCTION

[75] Inventors: Kazuhiko Hayashi, Saitama-ken; Chisato Sato, Kamifukuoka; Satoshi Tamai, Kawasaki; Takao Abe, Sakado; Takeshi Isoda, Sayama; Ado Mihira, Asaka; Toshio Kumagai, Kawagoe, all of Japan

[73] Assignee: Lederle (Japan), Ltd., Tokyo, Japan

[21] Appl. No.: 795,428

[22] Filed: Feb. 5, 1997

Related U.S. Application Data

[63] Continuation-in-part of Ser. No. 570,888, Dec. 12, 1995, Pat. No. 5,659,043, and Ser. No. 631,224, Apr. 12, 1996, Pat. No. 5,679,790, which is a division of Ser. No. 267,397, Jun. 29, 1994, Pat. No. 5,534,510.

[30] Foreign Application Priority Data

| Jul. 1, 1993 | [JP] | Japan | 5-213306 |
|---|---|---|---|
| Mar. 28, 1994 | [JP] | Japan | 6-79320 |
| May 12, 1994 | [JP] | Japan | 6-122046 |
| Dec. 12, 1994 | [JP] | Japan | 6-331423 |
| Sep. 11, 1995 | [JP] | Japan | 7-257281 |

[51] Int. Cl.$^6$ .................................................. C07D 417/04
[52] U.S. Cl. .................................................. 548/193
[58] Field of Search ............................................. 548/193

[56] References Cited

U.S. PATENT DOCUMENTS

| 5,102,997 | 4/1992 | Sugimura et al. | 540/350 |
|---|---|---|---|
| 5,534,510 | 7/1996 | Abe | 514/210 |

FOREIGN PATENT DOCUMENTS

| 0 160 391 | 11/1985 | European Pat. Off. . |
| 01 61 541 | 11/1985 | European Pat. Off. . |
| 0 632 039 | 1/1995 | European Pat. Off. . |
| 93/23402 | 11/1993 | WIPO . |

OTHER PUBLICATIONS

Patent Abstracts of Japan, vol. 13, No. 63, Feb. 13, 1989, JP 63-255280.
Chen, Bull Chem Soc. Japan III, (3) 762, 1968.

*Primary Examiner*—Robert Gerstl
*Attorney, Agent, or Firm*—Foley & Lardner

[57] ABSTRACT

A first embodiment of the invention relates to novel carbapenem compounds, (1R, 5S, 6S)-2-[1-(1,3-thiazolin-2-yl) azetidin-3-yl]thio-6-[(R)-1-hydroxy-ethyl]-1-methylcarbapen-2-em-3-carboxyic acid derivatives. These carbapenem compounds are represented by the following formula having a beta-coordinated methyl group introduced at the 1-position and a [1-(1,3-thia-zolin-2-yl)azetidin-3-yl] thio group introduced at the 2-position.

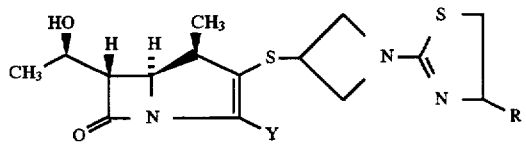

In the formula, R is hydrogen; lower alkyl group which is unsubstituted or substituted by hydroxy, lower alkoxy or lower alkoxy-lower alkoxy group; group —COOR$^1$ (R$^1$ is hydrogen or lower alkyl group); or group —CONR$^2$R$^3$ (R$^2$ and R$^3$ are, independently each other, hydrogen or lower alkyl), and Y is carboxy, —COO$^\ominus$ or protected carboxy. These compounds are useful antibiotics for prevention and treatment of bacterial infections.

The second embodiment of the invention relates to 3-mercapto-1-(1,3-thiazolin-2-yl)azetidine represented by the following formula and its acid addition salts

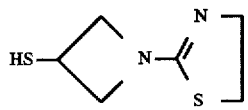

and to the production process therefor. The above compounds are useful as intermediates for preparing carbapenem compounds, which have strong antibacterial activity, with convenience and high yield.

16 Claims, No Drawings

SULFUR-CONTAINING COMPOUNDS METHOD FOR THEIR USE AND PRODCTION

This application is a continuation-in-part application, and claims priority under 35 U.S.C. § 120 of Ser. No. 08/570,888 filed Dec. 12, 1995 now U.S. Pat. No. 5,689,043 and Ser. No. 08/631,224 filed Apr. 12, 1996 now U.S. Pat. No. 5,679,790 which is a divisional application of Ser. No. 08/267,397 filed Jun. 29, 1994 now U.S. Pat. No. 5,534,510. All of those applications and patents are incorporated by reference in their entireties.

The substituent designation of the formulae according to the first embodiment are specific to the first embodiment and may be the same or different than the substituent designation of formulae of the second embodiment.

BACKGROUND OF THE FIRST EMBODIMENT OF THE INVENTION

1. Field of the Invention

The first embodiment of the invention relates to 2-[1-(1, 3-thiozolin-2-yl) azetidin-3-yl]thio-carbapenem derivatives.

The present invention relates to carbapenem antibiotics and, more particularly, to 1β-methyl-carbo-penem derivatives having a methyl group introduced at the 1-position and [1-(1,3-thiozolin-2-yl)azetidin-3-yl]thio group introduced at the 2-position of the carbapenem skeleton, and to antibacterial compositions containing the same as an active ingredient.

2. Description of the Prior Art

Heretofore, as various antibacterial substances, there have been proposed many carbapenem antibiotic substances having, as a basic skeleton, carba-2-penem-3-carboxylic acid represented by the following formula (A):

(A)

For example, an initial generation of carbepenem antibiotics is a naturally occurring carbepenem compound such as thienamycin represented by the formula (B):

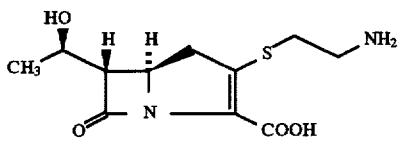

(B)

The thienamycin may be obtained from a fermentation broth of *Streotomyces cattleya* and has a broad range of antibacterial spectra against Gram-positive and Gram-negative bacteria. It has been expected therefore to be developed as a highly useful compound, but its poor chemical stability has precluded its commercialization.

With the foregoing background, many researchers have attempted to develop a carbapenem compound having antibacterial activities as high as thienamycin and ensuring more chemical stability. As a result, there has been developed imipenem (INN) represented by the following formula (C):

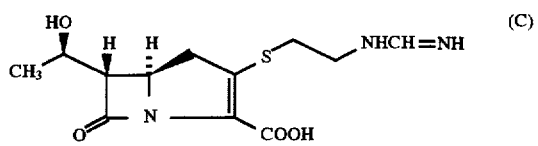

(C)

This compound is a practically available antibacterial agent and may be obtained by converting an amino group as a side chain at the 2-position to a formimidoyl group.

The imipenem of the formula (C) exhibits anti-bacterial activities higher than those of the thienamycin and ensures some degree of chemical stability; however, it presents the disadvantage that it is decomposed within a short period of time by kidney dehydropeptidase (DHP) in the living body. For this reason, it cannot be administered singly, and must be used in combination with a DHP inhibitor in order to control its decomposition leading to inactivation. Its formulation for clinical administration is a combination with cilastatin (INN) that is a DHP inhibitor.

An antibacterial agent preferred for practical clinical use, however, is one that alone can demonstrate antibacterial activity. Furthermore, the DHP inhibitor to be combined with the antibiotic could exert undesirable actions on tissues of the living body. For these reasons, the combined use should be avoided wherever possible. Thus there has been a growing demand for a carbapenem compound having sufficiently high degrees of both antibacterial activity and resistance to DHP.

Recently, there were proposed some carbapenem compounds of the type that could achieve the above objectives. Such carbapenem compounds are 1-methyl-carbapenem compounds in which a methyl group is introduced at the 1-position and various heterocyclyl-thio groups at the 2-position of the carbapenem skeleton. For example, Japanese Laid-Open Patent Publication No. 202,866/1985 to Sankyo discloses 2-heterocyclyl-thio-1-methylcarbapenem compounds including a compound having at the 2-position a (N-methylacetoimidoyl-azetidin-3-yl)thio substituent, represented by the formula (D):

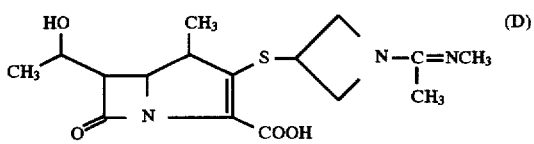

(D)

It is reported that this compound has superior antibacterial activities as well as a remarkably improved resistance to decomposition by DHP leading to inactivation so that it demonstrates highly useful effects; however, the Japanese Patent document does not provide any specific antibacterial data or working examples. Therefore, Sankyo does not disclose anything about carbapenem compounds having at the 2-position 1-(1,3-thiazolin-2-yl)azetidin-3-yl-thio substituent according to the present invention. Most recently, International Patent Publication Number WO 93/23,402 to Fujisawa disclosed 2-(3-azetidinylthio) carbapenem compounds represented by the following formula (E):

(E)

In the specification of this patent publication Fujisawa specifically discloses the carbapenem compounds represented by the following formula (F):

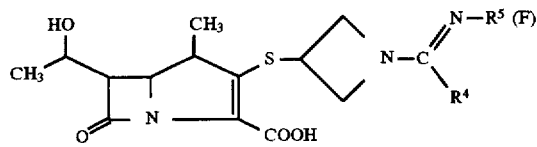

wherein $R^4$ and $R^5$ are combined together to form optionally substituted imino-containing heterocyclic group: however, among the compounds of formula (F), the only one compound is supported by working example, and there isn't any specific description of antibacterial data whatsoever. No specific compounds according to the present invention are disclosed therein, and any prior patent application mentioned above does not suggest anything about such compounds as having superior pharmacological characteristics as demonstrated and claimed in the present invention. Therefore, there was no anticipation of the specific compounds disclosed and claimed herein.

Carbapenem compounds possess a potent antibacterial activity with a broad spectrum. However, like other β-lactam antibacterial agents used in clinical practice, it is anticipated that carbapenem compounds will be uneffective against carbapenem-resistant bacteria. Accordingly, there have been proposed some carbapenem compounds having unique substituents at 2-position of the carbapenem skeleton. Furthermore, even though oral formulations of carbapenem compounds are useful for daily administration, the carbapenem antibiotics which have been proposed in prior patent application are mainly used for injectable formulation. Therefore, there has been a demand for orally administrable carbapenem antibiotics.

SUMMARY OF THE FIRST EMBODIMENT OF THE INVENTION

The present invention provides carbapenem compounds having high antibacterial activities, a strong action of inhibiting β-lactamase as well as improved resistance to kidney dehydropeptidase. More specifically, the present invention provides the carbapenem compounds substituted by a methyl group at the 1-position in the β-configuration, in which particularly a [1-(1,3-thiazolin-2-yl)azetidin-3-yl]thio group is introduced at the 2-position.

Accordingly, one object of the present invention is to provide (1R,5S,6S)-2-[1-(1,3-thiazolin-2-yl)azetidin-3-yl]thio-6-[(R)-1-hydroxyethyl]-1-methyl-carbapen-2-em-3-carboxylic acid derivative represented by the following formula:

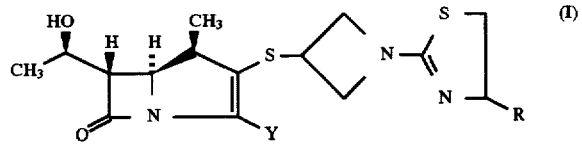

wherein R is hydrogen; lower alkyl group which is unsubstituted or substituted by hydroxy, lower alkoxy or lower alkoxy-lower alkoxy group; group —COOR$^1$ (R$^1$ is hydrogen or lower alkyl group); or group —CONR$^2$R$^3$ (R$^2$ and R$^3$ are, independently each other, hydrogen or lower alkyl).

Y is carboxy, —COO$^\ominus$ or protected carboxy, or a pharmaceutically acceptable salt thereof.

More specifically, the present invention provides (1R,5S,6S)-2-[1-(1,3-thiazolin-2-yl)azetidin-3-yl]-thio-6-[(R)-1-hydroxyethyl]-1-methyl-carbapen-2-em-3-carboxylic acid of the following formula:

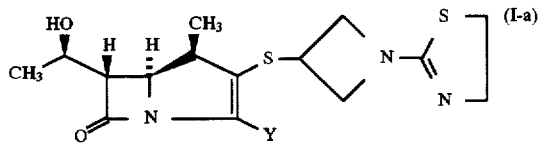

wherein Y has the same meaning as above, or a pharmaceutically acceptable salt thereof.

Still more specifically, the present invention provides (1R,5S,6S)-2-[1-(1,3-thiazolin-2-yl)azetidin-3-yl]thio-6-[(R)-1-hydroxyethyl]-1-methyl-carbapen-2-em-3-carboxylic acid of the following formula:

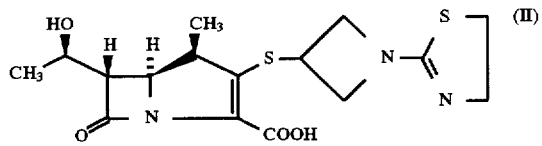

or a pharmaceutically acceptable salt thereof.

Another object of the present invention is to provide orally administrable carbapenem compounds which are converted into active carbapenem compounds of formula (II) in the body and show potent activities against a number of pathogenic microorganisms. For the above purpose of the invention, provided is (1R,5S,6S)-2-[1-(1,3-thiazolin-2-yl) azetidin-3-yl]thio-6-[(R)-1-hydroxyethyl]-1-methyl-carbapen-2-em-3-carboxylate of the following formula:

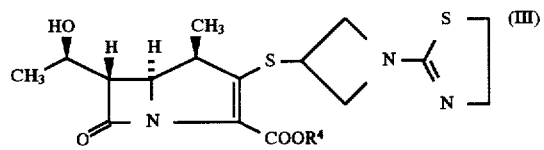

wherein R$^4$ is ester moiety of an esterified carboxy, or a pharmaceutically acceptable salt thereof.

Preferable orally administrable carbapenem compound of the present invention is 1-[(cyclohexyloxy)carbonyloxy] ethyl (1R,5S,6S)-2-[1-(1,3-thiazolin-2-yl)azetidin-3-yl]thio-6-[(R)-1-hydroxyethyl]-1-methyl-carbapen-2-em-3-carboxylate of the following formula:

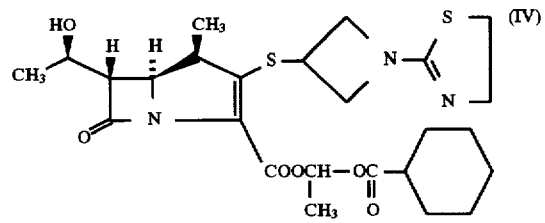

or a pharmaceutically acceptable salt thereof.

The other object of the present invention is to provide antibacterial compositions containing the carbapenem compounds represented by formula (I) or pharmaceutically acceptable salts thereof, as an active ingredient.

Preferable antibacterial composition is orally-administrable formulation containing the carbapenem compound of formula (IV).

DETAILED DESCRIPTION OF THE FIRST EMBODIMENT OF THE INVENTION

The carbapenem compounds according to the present invention are novel compounds that are not specifically disclosed in the prior patent publications (for instance, Japanese Patent Laid-Open Publication No. 202,886/1985, and WO 93/23,402). In particular, they are remarkably characterized in that the substituent at the 2-position of the carbapenem skeleton is a [1-(1,3-thiazolin-2-yl)azetidin-3-yl]thio group and in that they have superior antibacterial activities and resistance to DHP.

In the specification of the present application, the term "lower" qualifying a group of a compound means that the group or compound so qualified has from 1 to 7, preferably from 1 to 4, carbon atoms.

The term "alkyl" referred to herein stands for a straight-chained or branched-chain hydrocarbon group having preferably from 1 to 20 carbon atoms and may include, for example, methyl, ethyl, n-propyl, isopropyl, n-butyl, isobutyl, sec-butyl, tert.-butyl, n-pentyl, isopentyl, n-hexyl, isohexyl, n-heptyl, isoheptyl, octyl, isooctyl, monanyl, dodecanyl, pentadecanyl, eicosanyl or the like.

The term "alkoxy" referred to herein stands for an alkyloxy group in which the "alkyl" group has the meaning as mentioned above. Examples include methoxy, ethoxy, n-propoxy, isopropoxy, n-butoxy, isobutoxy, sec-butoxy, tert-butoxy, n-pentyloxy, isopentyloxy, n-hexyloxy, isohexyloxy, n-heptyloxy, isoheptyloxy or the like. Among them, methoxy, ethoxy, isobutoxy, sec-butoxy or tert-butoxy is preferably used.

The term "protected carboxy" is esterified carboxy which is represented by the group —COOR$^4$ (wherein R$^4$ is ester moiety of an esterified carboxy). Suitable ester moiety of an esterified carboxy represented by the group "R$^4$" is lower alkyl which may have at least one suitable substituent(s), and can be represented by the following group:

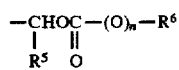

wherein R$^5$ is hydrogen or alkyl group,

R$^6$ is alkyl or cycloalkyl group in which these groups may be substituted by alkoxy, group: —OP(=O)(OR$^7$) (wherein R$^7$ is hydrogen, alkyl, aryl or aralkyl), carboxyl or propylglycinamide; and n is 0 or 1.

The term "aryl" may be monocyclic or polycyclic aryl group which may have at least one substituent(s) such as alkyl, for example, phenyl, tolyl, xylyl, α-naphthyl or β-naphthyl and the like.

Suitable "aralkyl" may include aryl substituted alkyl in which the "aryl" group and "alkyl" group have the meanings as mentioned above. Examples include benzyl, benzhydryl, trityl, phenethyl, α-methylbenzyl, phenylpropyl, naphthylmethyl and the like.

The term "cycloalkyl" may be saturated monocyclic hydrocarbon group having from 3 to 7 ring carbon atoms, and for example cyclopropyl, cyclobutyl, cyclopentyl, cyclohexyl, cycloheptyl or the like.

Therefore, suitable "ester moiety" is for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, or 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl (lower)alkyl ester (e.g. 2-mesylethyl ester, etc.), mono(or di or tri)halo(lower)alkyl ester (e.g. 2-iodoethyl ester, 2,2,2-trichloroethyl ester, etc.);

lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-)isopropoxycarbonyloxyethyl ester, etc.], cycloalkyloxycarbonyloxy(lower)alkyl ester (e.g. cyclohexyloxycarbonyloxymethyl ester, 1-(or 2-)cycloalkyloxycarbonyloxy ethyl ester, etc.), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; or the like. More preferable example of the protected carboxy thus defined may be pivaloyloxymethyloxycarbonyl or 1-(cyclohexyloxycarbonyl)ethyloxycarbonyl.

Typical examples of the compounds of formula (I) are shown in the following Table 1 and Table 2.

TABLE 1

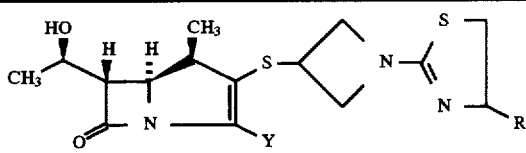

| R | Y |
|---|---|
| H | COOH |
| CH$_3$ | COOH |
| CH(CH$_3$)$_2$ | COOH |
| CH$_2$OH | COOH |
| CH$_2$OCH$_2$CH$_3$ | COOH |
| CH$_2$OCH$_2$OCH$_3$ | COOH |
| COOC$_2$H$_5$ | COOH |
| CON(CH$_3$)$_2$ | COOH |

TABLE 2

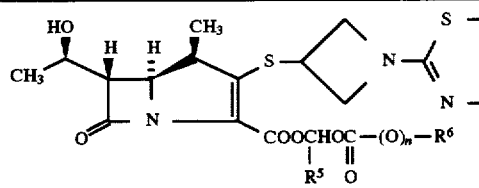

| R$^5$ | OC—(O)$_n$—R$^6$ ‖ O |
|---|---|
| H | OCCH$_3$ ‖ O |
| CH$_3$ | OCCH$_3$ ‖ O |
| C(CH$_3$)$_3$ | OCCH$_3$ ‖ O |
| H | OCCH$_2$OCH$_3$ ‖ O |

TABLE 2-continued

[Structure shown: bicyclic β-lactam with HO-CH(CH₃)-, CH₃, S-azetidine-N=C(S)(N-) substituent, and COOCHOC(-(O)ₙ-R⁶) group with R⁵ substituent]

OC—(O)ₙ—R⁶
||
O

| R⁵ | OC(O)ₙR⁶ group |
|---|---|
| CH₃ | OC(O)CH₂OCH(CH₃)₂ |
| H | OC(O)-cyclohexyl-H |
| (CH₂)₅CH₃ | OC(O)-cyclohexyl-H |
| H | OC(O)-cyclohexyl(H)-OCH₃ |
| H | OCC(CH₃)₃ (C=O) |
| C(CH₃)₃ | OCC(CH₃)₃ (C=O) |
| H | OCC₄H₉ (C=O) |
| H | OCC₇H₁₅ (C=O) |
| CH₃ | OCC₇H₁₅ (C=O) |
| H | OCC₁₅H₃₁ (C=O) |
| CH₃ | OCC₁₅H₃₁ (C=O) |
| H | OCCH₂CH₂OP(OH)₂ (C=O, P=O) |
| H | OCCH₂CH(CH₃)OP(OC₆H₅)₂ (C=O, P=O) |
| H | OC(O)-cyclohexyl(H)-OP(OH)₂(=O) |
| H | OP(OC₆H₅)₂ on cyclohexyl with OC(O)- |
| H | OC(CH₂)₃COOH (C=O) |
| CH₃ | OC(CH₂)₃COOH (C=O) |
| H | OC(O)-cyclohexyl-COOH |
| H | OC(CH₂)₇COOH (C=O) |
| CH₃ | OC(CH₂)₇COOH (C=O) |
| H | OC(CH₂)₅OP(OH)₂ (C=O, P=O) |
| CH₃ | OC(CH₂)₅OP(OH)₂ (C=O, P=O) |
| H | OC(CH₂)₃CNHCH₂C-N-prolyl-COOH (two C=O) |
| CH₃ | OC(CH₂)₇CNHCH₂C-N-prolyl-COOH (two C=O) |
| H | OCOCH₃ (C=O) |
| H | OCO(CH₂)₃OCH₃ (C=O) |

TABLE 2-continued

| $R^5$ | $OC-(O)_n-R^6$ $\parallel$ $O$ |
|---|---|
| H | $OCOCH_2CH_2OP(OCH_3)_2$ with C=O and P=O |
| H | OCO—⟨cyclohexyl-H⟩ (C=O) |
| $CH_3$ | OCO—⟨cyclohexyl-H⟩ (C=O) |
| H | $OCOC(CH_3)_3$ (C=O) |
| $CH_3$ | $OCOC_4H_9$ (C=O) |
| H | $OCOC_{15}H_{31}$ (C=O) |
| H | $OCO(CH_2)_3COOH$ (C=O) |
| H | OCO—⟨cyclohexyl-H⟩—$OP(OCH_3)_2$ (C=O, P=O) |

The pharmaceutically acceptable salts of the above listed compounds are also included in the examples of the compounds of the present invention.

Furthermore, when the compounds of the present invention have an asymmetric carbon in the side chain at the 2-position or 3-position, these optically active compounds can be stereo-selectively obtained by using the optically active starting materials (see the examples described below), or they can be also obtained by resolution of the diastereoisomeric mixture of these compounds by ordinary methods. Therefore, the optically active and stereoisomeric mixture of the compounds (I) should be included in the compounds of the present invention.

The compounds of the present invention of the formula (I) may be prepared in accordance with the processes as illustrated by the reaction schemes shown below.

The compound of formula (I) in which the group "Y" is carboxy or —COO$^\ominus$ may be prepared by the following Reaction Scheme A:

Reaction Scheme A

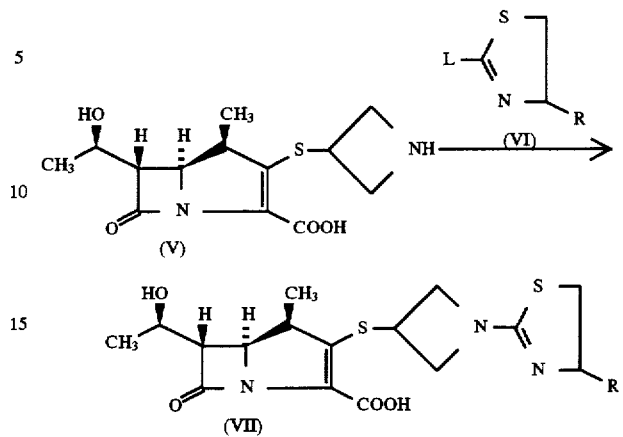

wherein L is a leaving group; and R has the same meaning as above.

The "leaving group" represented by L in the formula (VI) may, for example, be an azido group; a halogen atom such as chlorine, bromine or fluorine; lower alkanoyloxy group such as acetoxy or propionyloxy; sulfonyloxy group such as benzenesulfonyloxy, tosyloxy or methanesulfonyloxy; lower alkoxy group such as methoxy or ethoxy; lower alkylthio group such as methylthio or ethylthio.

The reaction of (1R,5S,6S)-2-[(azetidin-3-yl)]thio-6-[(R)-1-hydroxyethyl]-1-methyl-carbapen-2-em-3-carboxylic acid of formula (V) with the compound of formula (VI) may be carried out, for instance, by reacting the compound of formula (V) with the compound (VI) in an appropriate buffer-solvent of pH 5 to 7 such as a phosphate buffer solution, an acetate buffer solution, a citrate buffer solution, a morpholino-propane sulfonate buffer solution, an N-methylmorpholino phosphate buffer solution or the like. The reaction can be carried out by adding the compound of formula (VI) into the solution mixture of the compound of formula (V) and by stirring the reaction mixture for an appropriate time.

The quantity of the compound of formula (VI) is not critical and may vary appropriately in a range from approximately 1 to approximately 10 moles, preferably in a range from approximately 1 to approximately 5 moles, per mole of the compound of formula (V). If necessary, an organic solvent, alcohol such as methanol, ethanol or isopropanol; ether such as diethyl ether or tetrahydrofuran; acetonitrile; dimethylformamide; or dimethylacetamide can be used as the reaction solvent together with the above buffer solution. The reaction temperature is not limited to a particular range and many vary in a wide range according to the starting material of (VI) to be used. It may range generally from about −78° C. to about 50° C., preferably from about −20° C. to about 0° C. The reaction may be finished in approximately 5 minutes to approximately 5 hours.

The compounds of formula (V) to be employed as a starting compound in the above reaction are known compounds or may be prepared in accordance with the known method described in Japanese Patent Publication No. 255, 280/1988.

Furthermore, the compound of the present invention of the formula (I) in which the group "Y" is carboxy or —COO$^\ominus$ may also be prepared in accordance with the following Reaction Scheme B.

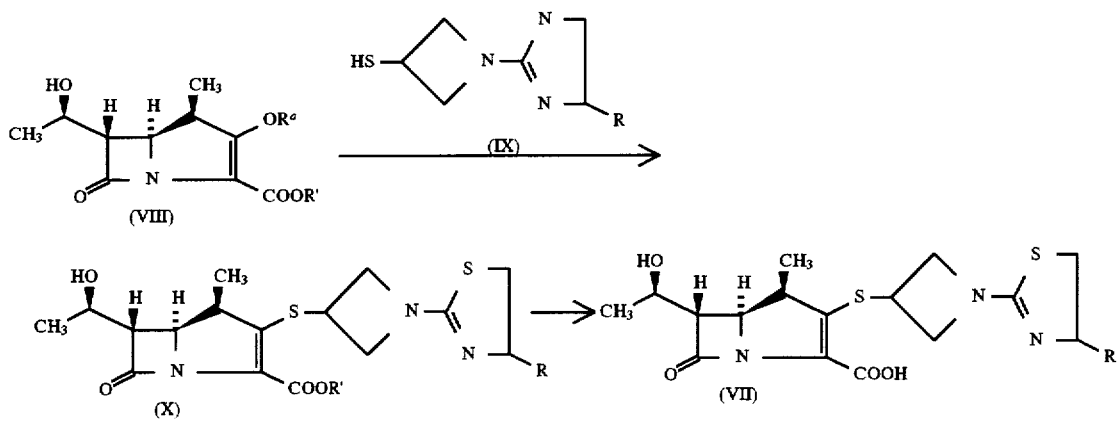

Reaction Scheme B wherein $R^a$ is an acyl group; R' is a carboxyl protecting group; and R has the same meaning as above.

The term "acyl group" represented by $R^a$ may be, in a narrower sense, a moiety obtainable by removing the hydroxyl group from the carboxyl group of an organic carboxylic acid as well as, in a broader sense, any acyl group derived from an organic sulfonic acid or an organic phosphoric acid. Such an acyl group may include, for example, a lower alkanoyl group such as acetyl, propionyl, butyryl or the like, a (halo)lower alkyl sulfonyl group such as methanesulfonyl, trifluoromethanesulfonyl or the like; a substituted or unsubstituted arylsulfonyl group such as benzenesulfonyl, p-nitrobenzenesulfonyl, p-bromobenzenesulfonyl, toluenesulfonyl, 2,4,6-triisopropylbenzenesulfonyl or the like; and diphenylphosphoryl.

The term "carboxyl protecting group" represented by R' stands for any group capable of protecting the carboxyl group of the compound involved without adversely affecting any other substituents and the reactions that follow and may include, for example, an ester residue such as a lower alkyl ester residue including, for example, methyl ester, ethyl ester, n-propyl ester, isopropyl ester, n-, iso-, sec- or tert-butyl ester, n-hexyl ester or the like; an aralkyl ester residue including, for example, benzyl ester, n-nitrobenzyl ester, o-nitrobenzyl ester, p-methoxybenzyl ester or the like; and a lower aliphatic acyloxymethyl ester residue including, for example, acetoxymethyl ester, propionyloxymethyl ester, n- or iso-butyryloxymethyl ester, pivaloxyloxymethyl ester or the like.

The reaction of the compound of formula (VIII) with [1-(1,3-thiazolin-2-yl)azetidin-3-yl]thiol of the formula (IX) may be carried out, for instance, by reacting the compound of formula (VIII) with the compound of formula (IX) in an amount ranging from approximately 0.5 molar to approximately 5 molar, preferably from approximately 0.8 molar to approximately 3 molar amount in an appropriate solvent such as tetrahydrofuran, dichloromethane, dioxane, dimethylformamide, dimethylsulfoxide; acetonitrile, hexamethylene phosphoramide or the like, preferable in the presence of a base such as sodium hydrogen carbonate, potassium carbonate, triethylamine, diisopropylethyl amine or the like at a temperature ranging from approximately −40° C. to approximately 25° C. for approximately 30 minutes to approximately 24 hours.

Preferably, the reaction may be carried out in an inert atmosphere, for example in an atmosphere of nitrogen gas or argon gas.

The reaction described above provides the compound of formula (X), and the resulting reaction mixture containing the compound of formula (X) may be used for the next reaction without further purification; or the compound (X) may be isolated from the reaction mixture by ordinary methods, if necessary.

In the reaction of the compound of formula (VIII) with the compound of formula (IX), another compound (IX') wherein the mercapto group of the formula (IX) is protected by a mercapto-protecting group may be used instead of the compound (IX). The reaction may be carried out in the following manner: the mercapto-protecting group of the compound (IX') is removed by ordinary methods used in the amino acid chemistry, then, without isolating the resulting compound (IX), to the reaction mixture the compound of formula (VIII) is added. The reaction condition is the same as above.

The carbapenem compounds of the present invention of the formula (VII) may be obtained by removal of the carboxyl protecting group R' of the compounds of the formula (X) obtained by the reaction method described above. The removal of the protecting group R' may be made by a reaction known per se for removing a protective group, such as solvolysis or hydrogenolysis. In a typical reaction, the compound represented by formula (X) may be treated, for instance, in a mixture of solvents such as tetrahydrofuran-water, tetrahydrofuran-ethanol-water, dioxane-water, dioxane-ethanol-water, n-butanol-water or the like containing a acetate buffer solution (pH 5.5), morpholino-propane sulfonic acid-sodium hydroxide buffer solution (pH 5.5), a phosphate buffer solution (pH 5.5), dipotassium phosphate, sodium bicarbonate or the like, using hydrogen under 1 to 4 atmospheric pressures, in the presence of a catalyst for hydrogenation such as platinum oxide, palladium-activated carbon or palladium hydroxide-activated carbon at temperatures ranging from approximately 0° C. to approximately 50° C. for approximately 0.25 to approximately 5 hours.

Furthermore, the removal of the protecting group R' of the compound of formula (X) may also be carried out by reacting the compound (X) with zinc in a buffer. In a typical reaction, the compound of formula (X) may be treated with zinc in an appropriate buffer solvent of pH 5 to 7 such as a phosphate buffer solution, an acetate buffer solution, a citrate buffer solution, a morphorinopropanesulfonate buffer solution, or an N-methylmorphorine buffer solution. Zinc used in the reaction may include, for example, elemental zinc in the form of powder, flower or granule or the like.

The amount of zinc used in this reaction is not strictly limited; however, in general, it is conveniently about 1 to 10 parts by weight, preferably 1 to 5 parts by weight per part by weight of the compound of formula (X) to be reacted.

In this reaction, an organic solvent may be used in combination. Examples of the solvent are alcohols such as ethanol, propanol and n-butanol; ethers such as diethyl ether and tetrahydrofuran; acetonitrile, dimethylformamide and dimethylacetamide. Usually, the reaction may be finished in approximately 5 minutes to approximately 5 hours in a reaction temperature from about −20° C. to about 50° C., preferably from the room temperature to about 30° C.

The compound of formula (VIII) to be employed as a starting compound in the above reaction is known per se and may be prepared in such a manner as disclosed, for example, in Japanese Laid-Open Patent Publication No. 123,985/1981 or, more preferably, in accordance with the stereo-selectivity method as disclosed in Japanese Laid-Open Patent Publication No. 284,176/1988.

Furthermore, [1-(1,3-thiazolin-2-yl)azetidin-3-yl]thiol of the formula (IX) may be prepared in accordance with the method described in the synthetic examples or working examples mentioned later, or may be easily prepared from commercially available compounds.

As a result, (1R,5S,6S)-2-[1-(1,3-thiazolin-2-yl)azetidin-3-yl]thio-6-[(R)-1-hydroxyethyl]-1-methylcarbapen-2-em-3-carboxylic acids represented by formula (I) in which "Y" is carboxy are produced in extremely high yield. These compounds may be isolated by using ion-exchange resins or polymer resins.

The present invention provides orally administrable ester derivatives of carbapenem compounds, that is, (1R,5S,6S)-2-[1-(1,3-thiazolin-2-yl)azetidin-3-yl]-thio-6-[(R)-1-hydroxyethyl]-1-methyl-carbapen-2-em-3-carboxylates of formula (I) in which the group "Y" is protective carboxy. The ester derivatives of the present invention of the formula (I) may be prepared in accordance with the following Reaction Scheme C:

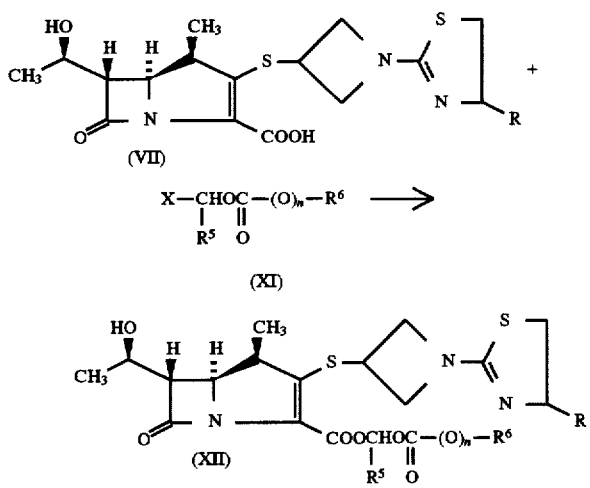

wherein X is halogen; and R, $R^5$, $R^6$ and n have the same meanings as above.

In the Reaction Scheme C, halogen represented by X may be chlorine, iodine, bromine or fluorine.

The reaction of (1R,5S,6S)-[1-(1,3-thiazolin-2-yl) azetidin-3-yl]thio-6-[(R)-1-hydroxyethyl]-1-methylcarbapen-2-em-3-carboxylic acid of formula (VII) with the compound of formula (XI) may be carried out, for instance, first by obtaining an alkali metal salt of formula (VII) in water by reacting the compound of formula (VII) with an appropriate alkali metal bases such as sodium hydroxide, potassium hydroxide, sodium carbonate, potassium carbonate, sodium bicarbonate, potassium bicarbonate or the like. Then, the alkali metal salt of formula (VII) thus obtained is reacted with the compound of formula (XI) in inert organic solvent, for example, ethers such as diethyl ether, tetrahydrofuran, dioxane; carbon hydrides such as benzene, toluene, xylene, cyclohexane; N,N-dimethylformamide, dimethylsulfoxide, acetonitrile, preferably in dimethylformamide under stirring.

The quantity of the alkali metal base is not critical and may vary appropriately in a range from approximately 1 to approximately 10 moles, preferably in a range from approximately 1 to approximately 5 moles, per mole of the compound (VII). The reaction temperature is not limited to a particular range and may vary from about 0° C. to room temperature. The reaction may be finished in approximately 2 or 3 minutes to approximately 1 hour under these conditions.

Furthermore, the quantity of the compound of formula (XI) is not critical and may vary appropriately in a range from approximately 1 to approximately 3 moles, preferably in a range from approximately 1 mole to approximately 1.5 moles, per mole of the alkali metal salt of formula (VII). The reaction temperature is not limited and generally may vary in a range from about −20° C. to about 50° C., preferably in a range from 0° C to room temperature, and the reaction may be finished in approximately 10 minutes to approximately 2–3 hours.

Thus, (1R,5S,6S)-2-[1-(1,3-thiazolin-2-yl)azetidin-3-yl] thio-6-[(R)-1-hydroxyethyl]-1-methyl-carbapen-2-em-3-carboxylates represented by the formula (I) in which Y is protected carboxy [compounds of formula (XII)] are produced and these compounds may be isolated and purified by usual method, for example, filtration, decantation, extraction, washing, removal of the solvent, column chromatography, thin-layer chromatography, recrystallization, distillation, sublimation or the like.

The compounds of formula (VII) to be employed as a starting compound in the above Reaction Scheme C can be prepared in accordance with the method described in the examples mentioned later.

The compounds of the present invention represented by formula (I) may be converted to a pharmaceutically acceptable acid addition salt thereof with inorganic or organic acids; these include, for example, aliphatic acid such as acetic acid, propionic acid, butyric acid, trifluoroacetic acid, trichloroacetic acid or the like; substituted or unsubstituted benzoic acid such as benzoic acid, p-nitrobenzoic acid or the like; lower(halo)alkylsulfonic acid such as methanesulfonic acid, trifluoromethanesulfonic acid or the like; substituted or unsubstituted arylsulfonic acid such as benzensulfonic acid, p-nitro benzenesulfonic acid, p-bromobenzenesulfonic acid, toluenesulfonic acid, 2,4,6-triisopropylbenzensulfonic acid or the like; organic phosphinic acid such as diphenylphosphinic acid; and inorganic acid such as hydrochloric acid, sulfuric acid, hydrobromic acid, hydriodic acid, borofluoric acid, nitrous acid or the like.

The desired compounds of formula (I) in accordance with the present invention are novel compounds that are not disclosed specifically in the above-mentioned publication and that are extremely stable against dehydropeptidase (DHP) known as a kidney enzyme and have superior antibacterial activities. Furthermore, the orally administrable carbapenem compounds of the present invention show good intestinal absorption in the body and easily converted to active carbapenem compound which is highly active against a number of pathogenic microorganisms. Therefore, the carbapenem compounds of the present invention of formula (I) in which the group Y is protective carboxy may be used as pro-drug type antibiotics for oral administration and are useful for practical clinical use. The remarkably high antibacterial activities, intestinal absorption and stability against the kidney DHP of the compounds of formula (I) according to the present invention have been determined by biological tests described below.

I. Antibacterial Tests
Test Procedures

The antibacterial activities were tested by an agar plate dilution method in accordance with the standard method of The Japanese Chemotherapy Society [Chemotherapy, Vol. 29, 76–79 (1981)].

A Mueller-Hinton (MH) agar liquid medium of a test microorganism was cultured overnight at 37° C. and the resultant culture medium was diluted with a buffered saline gelatin (BSG) solution to contain approximately $10^6$ cells of the test microorganisms per milliliter, and then the diluted solution was inoculated with a microplanter at the rate of approximately 5 microliters on a MH agar medium containing a test compound. This medium was then incubated at 37° C. for 18 hours. The minimum inhibitory concentration (MIC) is determined as a minimum concentration in which no test microorganism could grow. It is noted here that the test organisms used were all standard strains.

Results

Table 3 shows the test results. The test compounds used therein were the Compound (28) obtained in Example 2, which is the active compound of the Compound (33) obtained in Example 6, and the Compound (31) obtained in Example 4.

TABLE 3

MINIMUM INHIBITORY CONCENTRATIONS (MIC)

| | MIC (μg/ml) Test Compounds | |
|---|---|---|
| Test Organisms | (28) | (31) |
| S. aureus FDA209P JC-1 | 0.013 | 0.05 |
| S. aureus Terajima | ≦0.006 | ≦0.006 |
| S. aureus MS353 | ≦0.006 | 0.025 |
| S. pyogenes Cook | ≦0.006 | ≦0.006 |
| B. subtilis ATCC 6633 | 0.025 | 0.025 |
| M. luteus ATCC 9341 | 0.2 | 0.2 |
| E. coli NIHJ JC-2 | 0.013 | 0.05 |
| E. coli K-12 C600 | 0.1 | 0.2 |
| E. cloacae 963 | 0.05 | 0.2 |
| E. aerogenes ATCC 13048 | 0.1 | 0.39 |
| K. pneumoniae PCI-602 | 0.013 | 0.013 |
| S. typhimurium 11D971 | 0.025 | 0.1 |
| S. typhi 901 | ≦0.006 | 0.05 |
| S. paratyphi 1015 | 0.05 | 0.05 |
| S. schottmuelleri 8006 | 0.025 | 0.2 |
| S. enteritidis G14 | 0.39 | 0.2 |
| S. marcescens IAM 1184 | 0.05 | 0.39 |
| M. morganii IFO 3848 | 0.39 | 0.2 |
| P. mirabilis IFO 3849 | 0.39 | 0.78 |
| P. vulgaris OX-19 | 0.1 | 0.1 |
| P. vulgaris HX-19 | 0.1 | 0.39 |
| P. rettgeri IFO 3850 | 0.39 | 6.25 |

The foregoing results clearly demonstrate that the carbapenem compounds according to the present invention have superior antibacterial activities against Staphylococcus, Streptococcus, Klebsiella and Proteus.

II. Antibacterial Activities against Clinically Isolated Microorganism
Test Procedures 1. Strains of Test organisms The following strains clinically isolated freshly in Japan were used in this test.

| | |
|---|---|
| MRSA | 28 strains |
| S. epidermidis | 23 strains |
| E. faecalis | 16 strains |
| E. coli | 20 strains |
| E. cloacae | 14 strains |
| K. pneumoniae | 23 strains |
| S. marcescens | 27 strains |

2. The test was carried out by the agar plate dilution method in accordance with the standard method of The Japanese Chemotherapy Society. The minimum inhibitory concentration (MIC) was determined in substantially the same manner as the test procedures described in Test I.

Results

The Compound (28) obtained in Example 2 was used in this test. The control compounds used were ceftazidime (CAZ) as a cephalosporin compound, and imipenem as a carbapenem compound, which are widely used in clinical practice.

Table 4 shows the test results. In the table, 50% inhibitory concentrations $MIC_{50}$ against test strains are listed.

TABLE 4

$MIC_{50}$ against CLINICALLY ISOLATED MICROORGANISM (μg/ml)

| | Test Species | | |
|---|---|---|---|
| Test Compounds | MRSA | S. epidermidis | E. fasecalis |
| Compound (28) | 0.78 | 0.39 | 0.39 |
| Imipenem | 3.13 | 0.2 | 0.78 |
| CAZ | 100 | 12.5 | 25 |

| | Test Species | | |
|---|---|---|---|
| Test Compounds | E. coli* | E. cloacae | K. pneumoniae |
| Compound (28) | 0.05 | 0.1 | 0.025 |
| Imipenem | 0.78 | 0.2 | 0.2 |
| CAZ | 3.13 | 1.56 | 0.2 |

| | Test Species |
|---|---|
| Test Compounds | S. marcescens |
| Compound (28) | 0.2 |
| Imipenem | 1.56 |
| CAZ | 0.39 |

*In the case of E. coli, $MIC_{100}$ data are shown.

The foregoing results clearly demonstrate that the carbapenem compounds according to the present invention have superior antibacterial activities.

III. Stability Test against Renal Dehydropeptidase-1:
Test Procedures

The stability of the carbapenem compounds of the present invention was measured with a purified enzyme extracted from the swine kidney cortex. As a substrate, the compound was adjusted to give a final concentration of 35 μg/ml and was then added to the enzyme solution in 50 mM MOPS buffer (pH 7.0). The reaction mixture was incubated at 30°

C. for 2 hours and then diluted with an equal volume of methanol. The residual antibiotic activity in the supernatant after centrifugation at 1,000× g for 20 minutes was determined by a bioassay method by using Staphylococcus aureus Terajima. Standard curves were calculated by using inactivated enzyme as a control.

Compound (28) obtained in Example 2 below was used as a test compound and imipenem was used as a control compound.

Results

Table 5 below shows the results of the stability test of the compound according to the present invention and imipenem against swine renal dehydropeptidase-1.

TABLE 5

STABILITY TO SWINE RENAL DHP-1

| Test Compounds | 0 | 30 | 60 | 120 | 240 (min) |
|---|---|---|---|---|---|
| Compound (28) | 100 | 100 | 82.9 | 67.1 | 40.0 |
| Imipenem | 100 | 35 | 10 | 3 | 0 |

*Residual activity (%)

The stability test results against DHP-1 clearly show that the carbapenem compound according to the present invention was more stable than imipenem.

IV. In Situ Experiments on Absorption from Rat Intestinal Loop

Method 7-week-old male rats of Wistar strain were used after fasting overnight. After anesthetizing the animals with ether, the intestine was exteriorized and an acute loop of 30 cm length was prepared from the upper part of jejunum by ligature of both ends. 0.2% physiological saline solutions of the test compounds were injected at a dose of 20 mg/kg into the loop with a syringe, and the loop was returned. About 0.4 ml blood was taken from the vena jugularis at 10, 30, 60 and 120 minutes after dosing. Then the plasma concentrations of the test compounds or the active metabolite were measured by HPLC. And the area under the plasma concentration level-time curve (AUC) for 2 hours after administration was calculated.

As the test compounds, the Compounds (28), (32) and (33) obtained in the Examples 2, 5 and 6, respectively, were used.

Results

Table 6 shows the test results. In the table, the maximum concentrations of the test compounds in plasma (C max) and the AUCs (µg.hr/ml) are shown. After administration of the Compounds (32) and (33), these compounds were undetectable and the deesterified active compound [Compound (28)] was only detected. Therefore, in the cases of these compounds, the test results are shown as those of Compound (28).

TABLE 6

INTESTINAL ABSORPTION

| | Test Compounds | | |
|---|---|---|---|
| Test Items | (28) | (32) | (33) |
| C max (µg/ml) | 0.8 | 8.4 | 12.3 |
| AUC (µg · hr/ml) (0–2 hr) | 1.0 | 9.4 | 15.7 |

The foregoing results clearly show that the orally administrable carbapenem compounds of the present invention have superior intestinal absorption. That is, after administration of Compounds (32) and (33), these compounds were easily absorbed in the body and then quickly converted to the active carbapenem compound [Compound (28)].

V. Oral Absorption Study

Method 5-week-old male mice of ddY strain were used after fasting overnight. The test compounds in 1% physiological saline solution at a dose of 100 mg/kg were administered orally to a group of 2 mice. Blood was taken from the vena jugularis at 15, 30, 60 and 120 minutes after dosing. Then the concentrations of the test compounds or the active metabolite and the area under the plasma concentration level-time curve (AUC) were calculated in the same way mentioned above.

As the test compounds, the Compounds (28), (32) and (33) of the present invention obtained in the Examples 2, 5 and 6 were used.

Results

Table 7 shows the test results. In the table, the maximum concentrations of the test compounds in plasma (C max) and the AUCs (µg.hr/ml) are shown. After administration of the Compounds (32) and (33), these compounds were undetectable and the deesterified active compound [Compound (28)] was only detected. Therefore, in the cases of these compounds, the test results are shown as those of Compound (28).

TABLE 7

ORAL ABSORPTION (µg/ml)

| | Test Compounds | | |
|---|---|---|---|
| Test Items | (28) | (32) | (33) |
| C max (µg/ml) | 3.5 | 131.2 | 128.3 |
| AUC (µg · hr/ml ) (0–2 hr) | 5.0 | 147.8 | 150.2 |

From the in vivo test results, the orally administrable carbapenem compounds of the present invention showed a good oral absorption.

VI. Toxicity

Toxicological studies were carried out using a group of 10 male mice of CrjCD(SD) strain weighing from 20 to 23 grams. Solutions containing each of the carbapenem Compounds (28), (31), (32) and (33) of the present invention were administered subcutaneously to the mice and subjected to observations for one week.

The results have revealed that the group of mice to which the carbapenem compounds of the present invention had been administered in the amount of 500 mg/kg were alive without any abnormal findings.

As described above, the carbapenem compounds according to the present invention demonstrate a wider scope of antibacterial spectra than do conventional cephalosporin compounds, and remarkable antibacterial activities comparable to imipenem as well as an overwhelmingly higher resistance against DHP than imipenem.

Therefore, the carbapenem compounds of formula (I) according to the present invention permit a single administration without combination with any other compounds and without a risk of any side effect that might be caused in their combined use with a DHP inhibitor, unlike imipenem that was led for the first time to a practically useful antibacterial agent in combination with cilastatin acting as a DHP inhibitor. The carbapenem compounds are accordingly extremely useful as antibacterial agents for therapy and prevention of infectious diseases from various pathogenic organisms.

The carbapenem compound of formula (I) according to the present invention may be administered as an antibacterial agent to the human being and other mammalian animals in the form of a pharmaceutically acceptable composition containing an antibacterially effective amount thereof. The administration dose may vary in a wide range with ages, patients, weights and conditions of patients, forms or routes of administration, physicians' diagnoses or the like and may be orally, parenterally or topically administered, to adult patients usually in a standard daily dose range from approximately 200 to approximately 3,000 mg once or in several installments per day.

The pharmaceutically acceptable composition of the carbapenem compound of formula (I) according to the present invention may contain an inorganic or organic, solid or liquid carrier or diluent, which is conventionally used for preparation of medicines, particularly antibiotic preparations, such as an excipient, e.g., starch, lactose, white sugar, crystalline cellulose, calcium hydrogen phosphate or the like; a binder, e.g., acacia, hydroxypropyl cellulose, alginic acid, gelatin, polyvinyl pyrrolidone or the like; a lubricant, e.g., stearic acid, magnesium stearate, calcium stearate, talc, hydrogenated plant oil or the like; a disintegrator, e.g., modified starch, calcium carboxymethyl cellulose, low substituted hydroxypropyl cellulose or the like; or a dissolution aid, e.g., a non-ionic surface active agent, an anionic surface active agent or the like, and may be prepared into forms suitable for oral, parenteral or topical administration. The formulations for oral administration may include solid preparations such as tablets, coatings, capsules, troches, powders, fine powders, granules, dry syrups or the like or liquid preparations such as syrups or the like; the formulations for parenteral administration may include, for example, injectable solutions, drip-feed solutions, depositories or the like; and the formulations for topical administration may include, for example, ointments, tinctures, creams, gels or the like. These formulations may be formed by procedures known per se to those skilled in the art in the field of pharmaceutical formulations.

The carbapenem compounds of formula (I) according to the present invention are suitably administered in the form of oral or parenteral formulations, particularly in the form of oral formulations.

The production of the carbapenem compounds of the formula (I) according to the present invention will be described more in detail by way of working examples.

In the following description, the following symbols are used to have the particular meanings.

Me: methyl group
Et: ethyl group
Ac: acetyl group
Ph: phenyl group
PNB: p-nitrobenzyl group
PNZ: p-nitrobenzyloxycarbonyl group
i-Pr: isopropyl
t-But: tert.-butyl
Boc: t-butoxycarbonyl Preparation 1

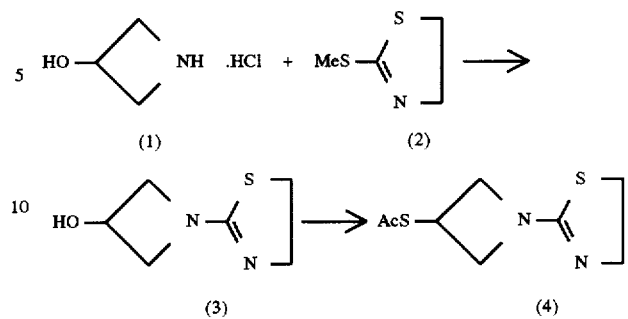

(a) To a solution of 109 mg of 3-hydroxyazetidine.HCl [Compound (1)] in 5 ml of ethanol was added a mixture of 133 mg of 2-methylthiazoline [Compound (2)] and sodium methoxide, and the reaction mixture was refluxed for 8 hours. After removal of the solvent under reduced pressure, the resulting residue was dissolved in chloroform and washed with 50% aqueous potassium carbonate solution. The solvent was removed under reduced pressure to give 119 mg (81.5%) of 3-hydroxy-1-(thiazolin-2-yl)azetidine [Compound (3)] as a crystaline.

$^1$H-NMR (CDCl$_3$) δ: 3.356 (t, 2H, J=7.26 Hz), 3.70–4.00 (m, 4H), 4.211 (t, 2H, J=8.21 Hz), 4.622–4.705 (m, 1H), 4.971 (s, 1H)

(b) To a mixture solution of triphenylphosphine and diethyl azodicarboxylate in 10 ml of tetrahydrofuran was added a mixture of 119 mg of Compound (3) and thioacetic acid under ice-cooling, and the reaction mixture was stirred for 1 hour at the same condition, then for 1 hour at room temperature. After the reaction solvent was removed under reduced pressure, the resulting residue was purified by silica gel column chromatography (chloroform:ethanol=1:1) to give 107 mg (65%) of 3-acetylthio-1-(thiazolin-2-yl)azetidine [Compound (4)].

$^1$H-NMR (CDCl$_3$) δ: 2.333 (s, 3H), 3.352 (t, 2H, J=7.26 Hz), 3.885 (dd, 2 H, J=8.24, 5.28 Hz), 4.012 (t, 2H, J=7.26 Hz), 4.250–4.374 (m, 1H), 4.426 (t, 2H, J=8.25 Hz)

Preparation 2

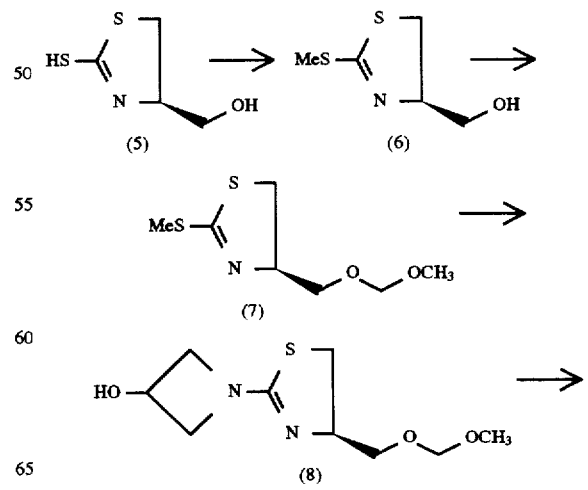

-continued

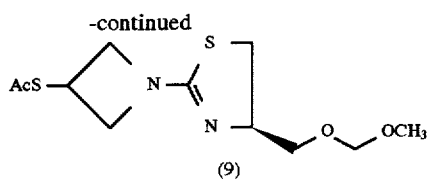

(a) To a mixture solution of 4.88 g of 4(R)-hydroxymethyl-2-mercapto-1,3-thiazoline [Compound (5)] and 22.8 ml of diisopropylethylamine in 65 ml of dry methanol was added 14.00 g of methyl iodide under refluxing condition, and the reaction mixture was refluxed for 1 hour. After removal of the solvent under reduced pressure, the resulting residue was dissolved in ethyl acetate and the organic layer was washed with saturated sodium bicarbonate solution, water and saturated saline solution and dried over magnesium sulfate. The solvent was removed under reduced pressure and the resulting residue was purified by silica gel column chromatography (chloroform-acetone) to give 3.14 g (59%) of 4(R)-hydroxymethyl-2-methylthio-1,3-thiazoline [Compound (6)].

$^1$H-NMR (CDCl$_3$) δ: 2.53 (s, 3H), 3.30 (dd, 1H, J=8.6, 10.6 Hz), 3.44 (dd, 1H, J=7.6, 10.6 Hz), 3.67–3.73 (m, 1H), 3.86–3.92 (m, 1H), 4.51–4.68 (m, 1H)

(b) 3.14 g of Compound (6) obtained in the step (a) and 6.7 ml of diisopropylethylamine were dissolved in 40 ml of dry dichloromethane solution. 2.33 g of chloromethylmethyl ether was added to the above mixture under ice-cooling and the reaction mixture was stirred for 1 hour under the same condition and for 15 hours at room temperature. After the reaction, the reaction mixture was washed with water, saturated sodium bicarbonate solution and saturated saline solution, and dried over magnesium sulfate. After removal of the solvent, the resulting residue was purified by silica gel column chromatography (chloroform-ethyl acetate) to give 1.42 g (36%) of 4(R)-methoxy-methyloxymethyl-2-methylthio-1,3-thiazoline [Compound (7)].

$^1$H-NMR (CDCl$_3$) δ: 2.55 (s, 3H), 3.35 (dd, 1 H, J=7.3, 10.9 Hz), 3.38 (s, 3H), 3.42 (dd, 1 H, J=8.3, 10.9 Hz), 3.474 (dd, 1H, J=7.6, 9.9 Hz), 3.78 (dd, 1H, J=5.0, 9.9 Hz), 4.66–4.70 (m, 1H), 4.67 (s, 2H)

(c) A mixture solution of 0.924 g of Compound (7) obtained in the above step (b), 0.540 g of 3-hydroxyazetidine.HCl [Compound (1)], 0.490 g of sodium bicarbonate and 0.160 g of acetic acid in 20 ml of ethanol was refluxed for 24 hours. After removal of the solvent, the resulting residue was dissolved in chloroform and washed with 50% potassium carbonate aqueous solution. The organic layer was dried over magnesium sulfate and then removed under reduced pressure. The resulting residue was purified by silica gel column chromatography (10% methanol in chloroform) to give 0.590 g (57%) of 1-(4(R)-methoxymethyloxymethyl-1,3-thiazolin-2-yl)-3-hydroxyazetidine [Compound (8)].

$^1$H-NMR (CDCl$_3$) δ: 3.25–3.32 (m, 1H), 3.37 (s 3H), 3.40–3.46 (m, 1H), 3.47–3.52 (m, 1H), 3.63 (dd, 1H. J=5.3, 9.9 Hz), 3.79–3.89 (m, 2H), 4.16–4.22 (m, 2H), 4.38–4.45 (m, 1H), 4.61–4.68 (m, 3H)

(d) To a solution of 1.40 g of triphenylphosphine in 15 ml of dry tetrahydrofuran was added 0.800 ml of diethyl azodicarboxylate under ice-cooling and the mixture solution was stirred for 0.5 hour. Then, a mixture solution of 0.588 g of Compound (8) obtained in the above step (c) and 0.361 ml of thioacetic acid in 15 ml of dry tetrahydrofuran was added dropwise to the above solution under ice-cooling and the reaction mixture was stirred for 1 hour under the same condition and for 1 hour at room temperature. After removal of the solvent, the resulting residue was purified by silica gel column chromatography (chloroform-acetone) to give 0.600 g (82%) of 2-acetyl-thio-1-(4(R)-methoxymethyloxymethyl-1,3-thiazolin-2-yl)azetidine [Compound (9)].

$^1$H-NMR (CDCl$_3$) δ: 2.33 (s, 3H), 329 (dd, 1H, J=6.3, 10.9 Hz), 3.37 (s 3H), 3.43 (dd, 1H, J=7.6, 10.9 Hz), 3.50 (dd, 1H, J=7.9, 9.9 Hz), 3.67 (dd, 1H, J=4.6, 9.9 Hz), 3.86–3.91 (m, 2H), 4.25–4.34 (m, 1H), 4.39–4.51 (m, 3H), 4.66 (s, 2H)

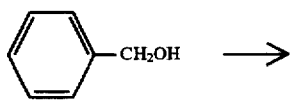

(10)

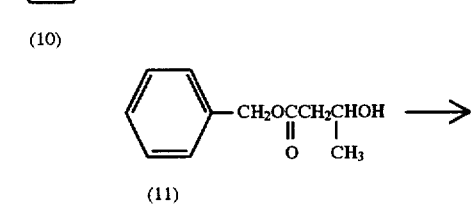

(11)

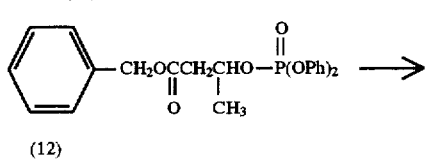

(12)

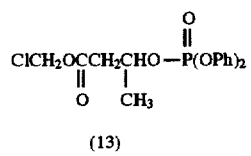

(13)

(a) 0.3 g of sodium hydroxide was added to 64.8 g of benzylalcohol and the reaction mixture was cooled to 0° C. To this reaction mixture was added 12.9 g of β-butyrolactone and the mixture was stirred for 5 minutes at 0° C. and for 2 hours at room temperature. After reaction, the reaction solution was neutralized by adding 15 ml of 1N-HCl solution and the separated organic layer was washed with saturated sodium bicarbonate aqueous solution and saline, and dried over magnesium sulfate. The resulting organic layer was distilled under reduced pressure to give 23.3 g (79%) of benzyl 3-hydroxybutanoate [Compound (11)] as oil.

Boiling point : 134° C./8 mmHg $^1$H-NMR (CDCl$_3$) δ: 1.22 (d, 3H, J=6.3 Hz), 2.41–2.58 (m, 2H), 2.95 (brs, 1H), 4.15–4.24 (m, 1H), 5.14 (s, 2H), 7.30–7.36 (m, 5H)

(b) A mixture solution of 1.0 g of benzyl 3-hydroxybutanoate obtained in the step (a), 1.0 ml of triethylamine and 63 mg of 4-dimethylaminopyridine in 10 ml of methylene chloride was cooled to 0° C. To this solution was added 1.79 g of diphenyl phosphorochloridate under nitrogen atmosphere and the reaction mixture was stirred for 3 hours at room temperature. After reaction, the reaction mixture was washed with 1N-HCl solution, saturated sodium bicarbonate aqueous solution and saline, and dried over magnesium sulfate. The solvent was removed under reduced pressure and the resulting residue was purified by silica gel column chromatography with methylene chloride to give 1.85 g (84%) of 3-diphenoxyphosphoryloxybutanoate [Compound (12)] as colorless oil.

$^1$H-NMR (CDCl$_3$) δ: 1.32 (d, 3H, J=6.3 Hz), 2.52 (dd, 1H, J=6.3 Hz, 15.8 Hz), 2.72 (dd, 1H, J=6.3 Hz, 15.8 Hz), 4.92

(d, 1H, J=12.9 Hz), 4.98 (d, 1H, J=12.9 Hz), 4.9-5.1 (m, 1H), 7.06-7.20 (m, 15H)

(c) To a solution of 1.23 g of Compound (12) obtained in the step (b), 8 ml of ethyl acetate and 8 ml of ethanol was added 61 mg of 10% palladium-carbon, and the reaction mixture was stirred for 1 hour under H₂ gas atmosphere at room temperature. Then, palladium-carbon was filtrated off and the organic layer was removed under reduced pressure. The resulting residue was dissolved in 8 ml of methylene chloride and to this solution was added a mixture of 847 mg of sodium bicarbonate, 8 ml of water, 98 ml of tetrabutylammonium phosphate and 570 mg of chloromethyl chlorosulfonate, and the reaction mixture was stirred for 2 hours at room temperature. After reaction, the organic layer was separated and washed with saline and dried over magnesium sulfate. The solvent was removed under reduced pressure and the resulting residue was purified by silica gel column chromatography with methylene chloride to give 1.10 g (99%) of chloromethyl 3-diphenylphosphoryloxybutanoate [Compound (13)] as colorless oil.

¹H-NMR (CDCl₃) δ: 1.46 (d, 3H, J=6.3 Hz), 2.66 (dd, 1H, J=6.3 Hz, 15.8 Hz), 2.85 (dd, 1H, J=6.3 Hz, 15.8 Hz), 5.09-5.18 (m, 1H), 5.58 (d, 1H, J=6.0 Hz), 5.61 (d, 1H, J=6.0 Hz), 7.16-7.37 (m, 10H)

Preparation 4

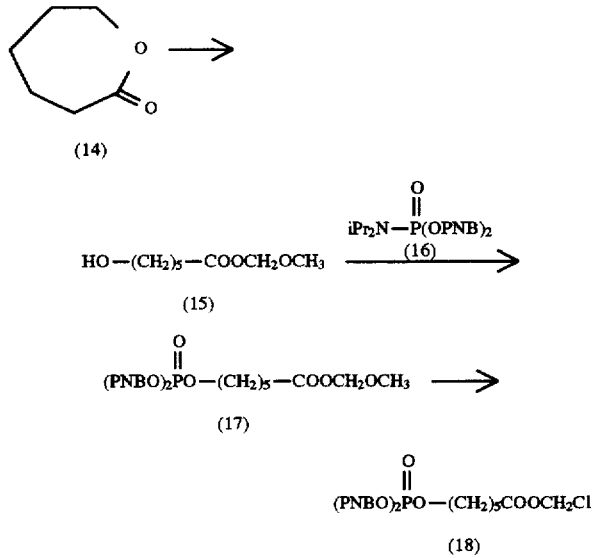

(a) To a solution of 12.0 g of ε-hexanolactone in 20 ml of ethanol was added a solution of 11.7 g of potassium hydroxide in 20 ml of water under ice-cooling and the reaction mixture was stirred for 2.5 hours at 40° C. After reaction, the reaction mixture was adjusted to pH 9 by adding 1N-HCl solution and washed with ethyl acetate (twice). The aqueous layer was concentrated under reduced pressure and the residue was adjusted to pH 1 by adding 1N-HCl solution and extracted by ethyl acetate. The organic layer was dried over magnesium sulfate and the solvent was removed under reduced pressure to give 11.5 g of 6-hydroxyhexanoic acid. A mixture of 1 g of 6-hydroxyhexanoic acid obtained above, 0.72 mg of sodium bicarbonate in 20 ml of water was stirred for 15 minutes. After reaction, the solvent was removed and the resulting residue was washed with acetonitrile to give 1.24 g of sodium 6-hydroxyhexanoic acid. Then, 276 mg of this compound was dissolved in 2.7 ml of dimethylformamide and to this solution was added 161 mg of methoxymethyl chloride and the reaction mixture was stirred for 1.5 hours at room temperature. After adding 10 ml of ethyl acetate to the reaction mixture, the organic layer was washed with saline, saturated sodium bicarbonate aqueous solution and saline respectively and dried over magnesium sulfate. The solvent was removed to give 190 mg (59%) of methoxymethyl 6-hydroxyhexanoate [Compound (15)].

¹H-NMR (CDCl₃) δ: 1.36-1.72 (m, 6H), 2.34 (t, 2H, J=7.2 Hz), 3.45 (s, 3H), 4.07 (t, 2H, J=6.7 Hz), 5.16 (s, 2H), 5.19 (s, 2H), 5.22 (s, 2H), 7.53 (d, 4H, J=8.7 Hz), 8.23 (d, 4H, J=8.7 Hz)

(b) To a solution of 25 g of phosphorus trichloride in 70 ml of diethyl ether was added dropwise during 30 minutes a mixture of 51 ml of diisopropylamine and 60 ml of diethyl ether at -10° C., then the reaction mixture was stirred for 1 hour at room temperature. After reaction, unsolved substance was filtrated off and the filtrate was distilled under reduced pressure to give 19.8 g (53%) of phosphorus diisopropylamino dichloride as oil. b.p. 57° C./4 mmHg.

To a solution of 2.06 g of phosphorus diisopropylamino dichloride in 40 ml of methylene chloride was added 4.19 ml of diisopropylamine at -30° C. under nitrogen atmosphere and 3.06 g of p-nitrobenzylalcohol was added. The reaction mixture was stirred for 0.5 hour at the same temperature and further 0.5 hour at room temperature. After removal of the solvent, the resulting residue was dissolved in 40 ml of diethyl ether and washed with saturated saline solution and dried over magnesium sulfate. The solvent was removed to give 4.50 g (100%) of diisopropylamino-di-p-nitrobenzylphosphite [Compound (16)] as yellowish solid.

¹H-NMR (CDCl₃) δ: 1.23 (d, 12H, J=6.6 Hz), 3.71 (q, 1H, J=6.6 Hz), 3.73 (q, 1H, J=6.6 Hz), 4.75-4.91 (m, 4H), 7.51 (d, 4H, J=8.2 Hz), 8.21 (d, 4H, J=8.2 Hz)

(c) A mixture solution of 100 mg of Compound (15) obtained in the step (a), 87.4 mg of tetrazole and 274 mg of Compound (16) obtained in the step (b) in 10 ml of methylene chloride was stirred for 1.5 hour at room temperature. Then, the reaction mixture was cooled to -40° C. and 215 mg of 3-chloroperbenzoic acid was added to the reaction mixture and the reaction mixture was stirred for 30 minutes. After reaction, the mixture was washed with saturated saline solution, 10% sodium thiosulfate aqueous solution, saturated sodium bicarbonate aqueous solution and saturated saline solution respectively. The organic layer was dried over magnesium sulfate and the solvent was removed under reduced pressure to give 306 mg (95%) of methoxymethyl 6-di-p-nitrobenzyloxy phosphoryloxyhexanoate [Compound (17)].

¹H-NMR (CDCl₃) δ: 1.36-1.72 (m, 6H), 2.34 (t, 2H, J=7.2 Hz), 3.45 (s, 3H), 4.07 (t, 2H, J=6.8 Hz), 5.16 (s, 2H), 5.19 (s, 2H), 5.22 (s, 2H), 7.53 (d, 4H, J=8.7 Hz), 8.23 (d, 4H, J=8.7 Hz)

(d) To a solution of 206 mg of Compound (17) obtained in the step (c) above in 2 ml of tetrahydrofuran was added 1 ml of 4N-HCl solution and the reaction mixture was stirred for 1.5 hour at room temperature. After reaction, the reaction mixture was adjusted to pH 1 by adding 1N-NaOH solution and washed with diethyl ether. Then, the water layer was adjusted to pH 1 by adding 1N-HCl solution and extracted with ethyl acetate. The organic layer was dried over magnesium sulfate and the solvent was removed to give 96 mg (51%) of 6-di-p-nitrobenzyloxy-phosphoryloxyhexanoic acid. Then, 96 mg of this hexanoic acid was dissolved in 4.8 ml of methylene chloride and to this solution was added a mixture solution of 51.3 mg of sodium bicarbonate in 4.8 ml of water, 6.6 mg of tetrabutylammonium hydrogen sulfate and 40.4 mg of chloromethyl chlorosulfonate, and the reaction mixture was stirred for 1 hour at room temperature.

After reaction, the organic layer was separated and washed with saturated sodium bicarbonate aqueous solution and saline, and dried over magnesium sulfate. After removal of the solvent under reduced pressure, the resulting residue was purified by silica gel column chromatography (methylene chloride-acetone) to give 69 mg (55%) of chloromethyl 6-di-p-nitrobenzyloxyphosphoryloxyhexanoate [Compound (18)].

¹H-NMR (CDCl₃) δ: 1.37~1.71 (m, 6H), 2.37 (t, 2H, J=7.2 Hz), 4.07 (t, 2H, J=6.6 Hz), 5.16 (s, 2H), 5.19 (s, 2H), 5.69 (s, 2H), 7.54 (d, 4H, J=8.5 Hz), 8.23 (d, 4H, J=8.5 Hz)

Preparation 5

HOOC—(CH₂)₇—COOH ⟶ PNBOOC—(CH₂)₇—COOCH₂Cl

(19)　　　　　　　　　　(20)

To a solution of 10 g of azelaic acid in 200 ml of acetonitrile were added 16.2 mg of triethylamine and 11.4 g of p-nitrobenzylbromide at nitrogen atmosphere under ice-cooling and the reaction mixture was stirred for 3 hours. After reaction, the reaction mixture was concentrated and 100 ml of water was added. The solution was adjusted to pH 2 by adding 1N-HCl solution and extracted 50 ml of ethyl acetate (twice). The organic layer was washed with saturated saline solution and dried over magnesium sulfate. The solvent was removed under reduced pressure and the resulting residue was purified by silica gel column chromatography (methylene chloride-methanol) to give 4.51 g (26%) of mono-p-nitrobenzylazelate. Then, to a solution of 550 mg of this azelate in 10 ml of methylene chloride were added 428 mg of sodium bicarbonate in 10 ml of water, 57 mg of tetrabutylammonium hydrogen sulfate and 336 mg of chloromethyl chlorosulfonate, and the reaction mixture was stirred vigorously for 2 hours at room temperature. After reaction, the reaction mixture was washed with saturated sodium bicarbonate aqueous solution and saturated saline solution, and dried over magnesium sulfate. After removal of the solvent, the resulting residue was purified by silica gel column chromatography (methylene chloride) to give 450 mg (74%) of p-nitrobenzyl chloromethylazelate [Compound (20)].

¹H-NMR (CDCl₃) δ: 1.20~1.40 (m, 10H), 2.37 (t, 2H, J=7.3 Hz), 2.39 (t, 2H, J=7.2 Hz), 5.20 (s, 2H), 5.70 (s, 2H), 7.51 (d, 2H, J=8.7 Hz), 8.23 (d, 2H, J=8.7 Hz)

Preparation 6

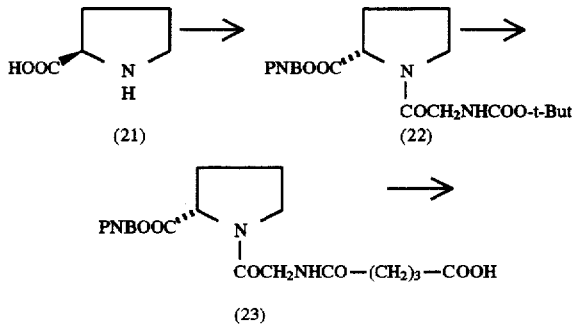

-continued

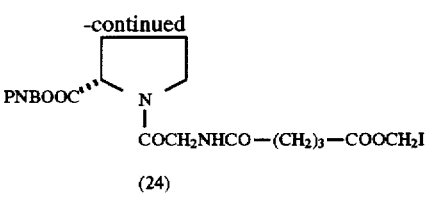

(24)

(a) A mixture solution of 5.0 g of L-proline, 9.91 g of p-toluenesulfonic acid monohydrate and 6.65 g of p-nitrobenzyl alcohol in 100 ml of benzene was refluxed for 2 days by using Dean-Stark trap. After reaction, the solvent was removed under reduced pressure and the resulting residue was washed with diethyl ether to give 21.7 g of L-proline p-nitrobenzyl ester p-toluenesulfonic acid salt as oil. Then, a mixture solution of 12.17 g of Boc-glycine and 13.32 g of 1-ethyl-3-(3-dimethylaminopropyl) carbodiimide.hydrochloride in 150 ml of ethylene chloride was stirred for 25 minutes under ice-cooling at nitrogen atmosphere. To this reaction mixture was added a solution of 29.36 g of the compound obtained above in 100 ml ethylene chloride and the reaction mixture was stirred overnight at room temperature. After reaction, the reaction mixture was washed with 10% citric acid aqueous solution, 4% sodium bicarbonate aqueous solution and saline, and dried over magnesium sulfate. The solvent was removed under reduced pressure and the resulting residue was purified by silica gel column chromatography (chloroform-methanol) to give 8.00 g of [N-(t-butoxycarbonyl)glycyl]L-proline p-nitrobenzyl ester [Compound (22)].

¹H-NMR (CDCl₃) δ: 1.45 (s, 9H), 1.96~2.33 (m, 4H), 3.43~3.70 (m, 2H), 3.93~4.01 (m, 2H), 4.59 (d, 1H, J=40 Hz, 8.6 Hz), 5.23 (d, 1H, J=13.5 Hz), 5.30 (d, 1H, J=13.5 Hz), 5.37 (br, 1H), 7.52 (d, 2H, J=8.9 Hz), 8.23 (d, 2H, J=8.9 Hz)

(b) To a solution of 4.10 g of Compound (22) obtained in the step (a) in 5 ml of methylene chloride was added 2.5 ml of trifluoroacetic acid under ice-cooling and the reaction mixture was stirred for 1 hour, then, 4 ml of trifluoroacetic acid was added to the reaction mixture and the stirring was continued for 2 hours. After reaction, the solvent was removed to give 5.82 g of glycyl-L-proline p-nitrobenzyl ester trifluoroacetic acid salt as pale brownish oil.

Then, to an ice-cooled solution of 5.54 g of the compound obtained above and 1.499 g of glutaric anhydride in 50 ml of methylene chloride was added 1.83 ml of triethylamine, and the reaction mixture was stirred for 20 minutes at the same temperature. After reaction, 60 ml of 10% citric acid aqueous solution and 200 ml of ethyl acetate were added to the reaction mixture and the organic layer was separated. The organic layer was extracted with 300 ml of 4% sodium bicarbonate aqueous solution, and the extraction was adjusted to pH 4 and extracted with ethyl acetate. The organic solvent was removed under reduced pressure to give 3.43 g of [N-(4-carboxybutanoyl)glycyl]-L-prolin p-nitrobenzyl ester [Compound (23)] as pale yellowish oil.

¹H-NMR (CDCl₃) δ: 1.90~2.20 (m, 3H), 1.97 (quintet, 2H, J=7.3 Hz), 2.20~2.34 (m, 1H ), 2.41 (t, 2H, J=7.3 Hz), 2.44 (t, 2H, J=7.3Hz), 3.53~3.75 (m, 2H), 4.04 (dd, 1H, J=4.3 Hz, 17.5 Hz), 4.22 (dd, 1H, J=4.9 Hz, 17.5 Hz), 4.58 (dd, 1H, J=4.0 Hz, 8.9 Hz), 5.20 (d, 1H, J=13.5 Hz), 5.32 (d, 1H, J=13.5 Hz), 6.85 (br, 1H), 7.50 (d, 2H, J=8.6 Hz), 8.22 (d, 2H, J=8.6 Hz)

(c) To a solution of 3.09 g of Compound (23) obtained in the step (b) in 70 ml of methylene chloride were added 1.85 g of sodium bicarbonate in 70 ml of water, 249 mg of tetrabutylammonium hydrogen sulfate and 1.57 g of ClCH₂SO₃Cl, and the reaction mixture was stirred for 140 minutes at room temperature. After reaction, the organic layer was separated and washed with 4% sodium bicarbonate aqueous solution and saline, and dried over magnesium sulfate. The solvent was removed under reduced pressure to give 3.00 g of [N-(4-chloromethyloxycarbonylbutanoyl) glycyl]-L-proline p-nitrobenzyl ester as pale yellowish oil. Then, a mixture solution of 2.86 g of the compound obtained above and 1.83 g of sodium iodide in 20 ml of acetonitrile was refluxed for 2 hours. After reaction, the solvent was removed and the resulting residue was dissolved in 70 ml of ethyl acetate. The organic layer was washed with 0.1N sodium thiosulfate aqueous solution and saline, and dried over magnesium sulfate. The solvent was removed under reduced pressure and the resulting residue was purified by silica gel column chromatography (methylene chloride-acetone) to give 2.35 g of [N-(4-iodomethyloxycarbonylbutanoyl)glycyl]-L-proline P-nitrobenzyl ester [Compound (24)] as yellowish oil.

¹H-NMR (CDCl₃) δ: 1.92~2.17 (m, 5H), 2.17~2.37 (m, 1H), 2.33 (t, 2H, J=7.3 Hz), 2.42 (t, 2H, J=7.3 Hz), 3.46~3.74 (m, 2H), 4.02 (dd, 1H, J=4.0 Hz, 17.8 Hz), 4.12 (dd, 1H, J=4.4 Hz, 17.8 Hz), 4.59 (dd, 1H, J=4.0 Hz, 8.9 Hz), 5.24 (d, 1H, J=13.5 Hz), 5.32 (d, 1H, J=13.5 Hz), 5.91 (s, 2H), 6.45 (br, 1H), 7.53 (d, 2H, J=8.9 Hz), 8.24 (d, 2H, J=8.9 Hz)

EXAMPLE 1

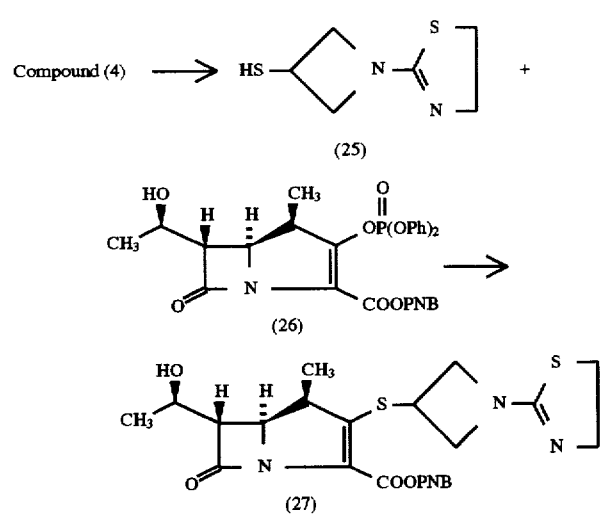

770 mg of 28% sodium methoxide-methanol solution was added to a mixture solution of 862 mg of Compound (4) obtained in the step (c) of Preparation 1 in 20 ml of anhydrous methanol under ice-cooling and nitrogen gas stream. Then the reaction mixture was stirred for 10 minutes under the same conditions. After reaction, 4 ml of 2N-HCl was added to the reaction mixture and the solvent was removed under reduced pressure to give the crude Compound (25). Then, the crude Compound (25) was dissolved in the mixture solution of anhydrous aceton-chloroform and to this solution were dded 2430 mg of p-nitrobenzyl (1R, 5S,6S)-2-(diphenylphosphoryloxy)-6-[(R)-1-hydroxyethyl]-1-methyl-carbapen-2-em-3-carboxylate [Compound (26)] and 2.8 ml of diisopropylethylamine under ice-cooling and nitrogen gas stream. After stirring the reaction mixture for 2 hours under the same conditions, ethyl acetate was added and the separated organic layer was washed with saturated sodium bicarbonate aqueous solution and saturated saline solution. The solvent was removed and the resulting residue was purified by silica gel column chromatography with chloroform:aceton (1:2) to give 1339 mg (65% from Compound (4)) of p-nitrobenzyl (1R,5S,6S)-2-[1-(thiazolin-2-yl) azetidin-3-yl]-thio-6-[(R)-1-hydroxyethyl]-1-methyl-carbapen-2-em-3-carboxylate [Compound (27)].

¹H-NMR (CDCl₃) δ: 1.235 (d, 3H, J=7.26 Hz), 1.349 (d, 3H, J=6.27 Hz), 3.160 (quintet, 1H, J=7.26 Hz), 3.265 (dd, 1H, J=2.3, 6.26 Hz), 3.367 (t, 2H, J=7.26 Hz), 3.898–4.038 (m, 4H), 4.071–4.147 (m, 1H), 4.212–4.278 (m, 2H), 4.372 (2H, J=7.92 Hz), 5.255 & ʊ 5.517(d (A B), 2H, J=13.85 Hz), 7.665 (d, 2H, J=8.58 Hz), 8.226 (d, 2H, J=8.58 Hz)

EXAMPLE 2

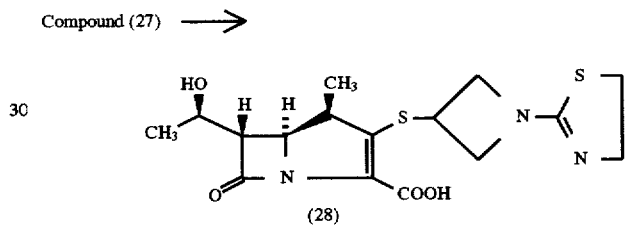

To a mixture solution of 1339 mg of Compound (27) obtained in Example 1 in 2 ml of tetrahydrofuran were added 60 ml of 0.38M phosphate buffer solution and 11.2 g of zinc powder, and the reaction mixture was vigorously stirred for 2 hours. After the reaction, unsolved substance was removed by using Celite® and the filtrate was washed with ethylacetate and the pH of the filtrate was adjusted to 5.5. Then, the filtrate was concentrated and the resulting residue was purified by using Diaion HP-40R column (5% isopropylalcohol-water) to give 630 mg (64%) of (1R,5S, 6S)-2-[1-(thiazolin-2-yl)azetidin-3-yl]thio-6-[(R)-1-hydroxyethyl]-1-methyl-carbapen-2-em-3-carboxylic acid [Compound (28)].

¹H-NMR (D₂O) δ: 1.093 (d, 3H, J=6.93 Hz), 1.207 (d, 3H, J=6.27 Hz), 3.05~3.20 (m, 1H), 3.357 (dd, 1H, J=2.3, 5.94 Hz), 3.558 (t, 2H, J=7.26 Hz), 3.920 (t, 2H, J=7.26 Hz), 4.00–4.20 (m, 5H), 4.20–4.30 (m, 1H), 4.60–4.70 (m, 1H)

IR (KBr): 1740, 1640, 1590 cm⁻¹

EXAMPLE 3

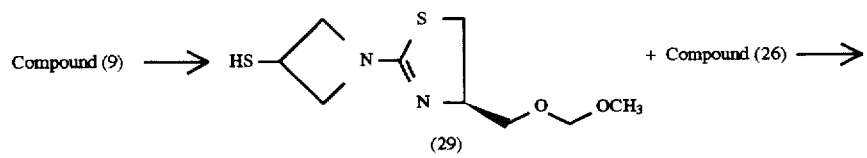

-continued

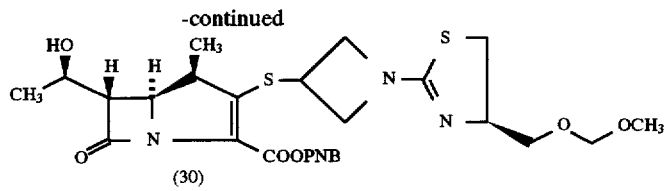

To a solution of 600 mg of Compound (9) obtained in the step (d) in Preparation 2 in 10 ml of anhydrous methanol was added 400 mg of 28% sodium methoxide-methanol solution under ice-cooling and nitrogen atmosphere, and the reaction mixture was stirred for 5 minutes under the same conditions. After the reaction, 0.355 ml of acetic acid was added and the solvent was removed under reduced pressure. The resulting residue was dissolved in 5 m of anhydrous acetonitrile and the unsolved substance was removed by filtration. Then, this filtrate was added to a solution of 1.230 g of p-nitrobenzyl (1R,5S,6S)-2-(diphenylphosphoryloxy)-6-[(R)-1-hydroxyethyl]-1-methyl-carbapen-2-em-3-carboxylate [Compound (26)] in 5 ml of anhydrous acetonitrile under ice-cooling, and 2.2 ml of diisopropylethylamine was further added dropwise to the reaction mixture. After stirring the reaction mixture for 1.5 hour under the same condition. The solvent was removed under reduced pressure. The resulting residue was dissolved in ethyl acetate and the organic layer was washed with saturated sodium bicarbonate aqueous solution, and dried over magnesium sulfate. After removal of the solvent, the resulting residue was purified by silica gel column chromatography (chloroform-acetone) to give 0.788 g (64% from Compound (26)) of p-nitrobenzyl (1R,5S,6S)-2-[1-(4(R)-methoxymethyloxymethyl-1,3-thiazolin-2-yl)azetidin-3-yl]thio-6-[(R)-1-hydroxyethyl]-1-methyl-carbapen-2-em-3-carboxylate [Compound (30)].

$^1$H-NMR (CDCl$_3$) δ: 1.24 (d, 3H, J=7.3 Hz), 1.36 (d, 3H, J=6.3 Hz), 3.16 (dq, 1H, J=7.3, 9.2 Hz), 3.25–3.34 (m, 2H), 3.37 (m, 2H), 3.43–3.47 (m, 1H), 3.51 (dd, 1H, J=7.9, 9.9 Hz), 3.67 (dd, 1H, J=5.0, 9.9 Hz), 2.94–4.00 (m, 2H), 4.07–4.17 (m, 1H), 4.23 (dd, 1H, J=2.6, 9.2 Hz), 4.20–4.30 (m, 1H), 4.30–4.51 (m, 3H), 4.66 (s, 2H), 5.25 (d, 1H, J=13.9 Hz), 5.51 (d, 1H, J=13.9 Hz), 7.66 (d, 2H, J=8.6 Hz), 8.23 (d, 2H, J=8.6 Hz)

EXAMPLE 4

415 mg (71%) of (1R,5S,6S)-2-[1-((4R)-methoxymethyloxymethyl-1,3-thiazolin-2-yl)azetidin-3-yl]thio-6-[(R)-1-hydroxyethyl]-1-methyl-carbapen-2-em-3-carboxylic acid [Compound (31)].

$^1$H-NMR (D$_2$O) δ: 1.10 (d, 3H, J=7.3 Hz), 1.21 (d, 3H, J=6.6 Hz), 3.06–3.18 (m, 1H), 3.22–3.33 (m, 1H), 3.33 (s, 3H), 3.36–3.47 (m, 1H), 3.61–3.75 (m, 3H), 4.09–4.31 (m, 6H), 4.33–4.56 (m, 1H), 4.60–4.68 (m, 3H)

IR (KBr: 1735, 1640, 1580 cm$^{-1}$

EXAMPLE 5

Compound (28) ⟶

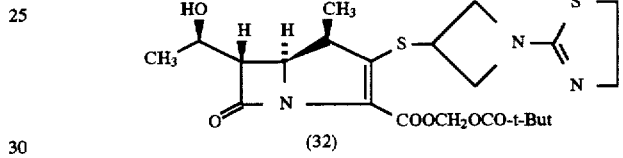

A mixture solution of 430 mg (1.12 mM) of Compound (28) obtained in the Example 2 and 94.1 mg (1.12 mM) of sodium bicarbonate in 15 ml of water was lyophilized. The resulting amorphous solid was dissolved in 5 ml of dimethylformamide, and 285 mg (1.18 mM) of pivalic acid iodomethyl ester was added to this solution and the reaction mixture was stirred for 1 hour at room temperature. After reaction, ethyl acetate was added to the reaction mixture and the organic layer was washed with saturated sodium bicarbonate aqueous solution and saline, and dried over magnesium sulfate. After removal of the solvent, the resulting residue was purified by silica gel column chromatography (10% methanol-chloroform) to give 415 mg of (74.6%) of pivaloyloxymethyl (1R,5S,6S)-2-[1-(1,3-thiazolin-2-yl)azetidin-3-yl]thio-6-[(R)-1-hydroxyethyl]-1-methyl-carbapen-2-em-3-carboxylate [Compound (32)].

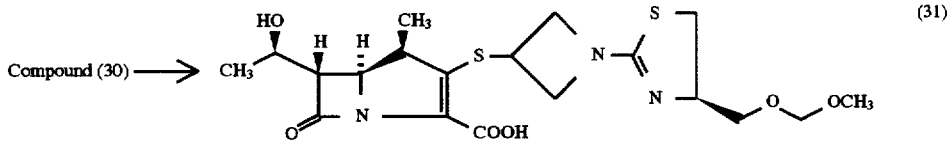

To a solution of 756 mg of Compound (30) obtained in Example 3 in 10 ml of tetrahydrofuran and 30 ml of 0.35M phosphate buffer (pH 6.0) solution was added 6.0 g of zinc powder, and the reaction mixture was stirred for 2 hours at room temperature. After removal of the zinc powder by filtration, the filtrate was washed with ethyl acetate and the pH of the filtrate was adjusted to 5.5, then the filtrate was concentrated. The resulting residue was purified by using Diaion HP-40R column (10% isopropanol-water) to give $^1$H-NMR (CDCl$_3$) δ: 1.229 (s, 9H), 1.229 (d, 3H, J=7.3 Hz), 1.339 (d, 3H, 6.3 Hz), 3.165 (dd, 1H, J=7.3 Hz, 9.2 Hz), 3.227 (dd, 1H, J=2.6 Hz, 6.9 Hz), 3.369 (t, 2H, 7.3 Hz), 3.952 (dd, 2H, 5.6 Hz, 8.6 Hz), 3.988–4.043 (m, 2H), 4085–4.162 (m, 1H), 4.183–4.274 (m, 2H), 4.346–4.426 (m, 2H), 5.842 (d, 1H, J=5.6 Hz), 5.972 (d, 1H, J=5.6 Hz)

EXAMPLE 6

Compound (28) ⟶

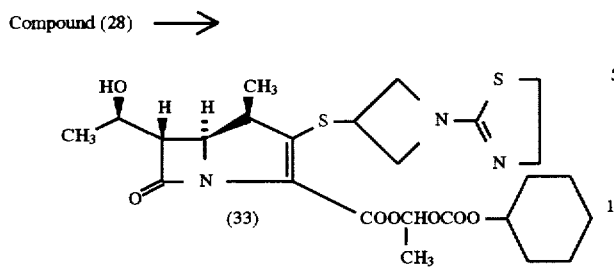

A mixture solution of 500 mg (1.30 mM) of Compound (28) obtained in the Example 2 and 109.4 mg (1.30 mM) of sodium bicarbonate in 15 ml of water was lyophilized. The resulting amorphous solid was dissolved in 5 ml of dimethylformamide, and 379.5 mg (1.30 mM) of 1-iodoethylcyclohexylcarbonate [prepared by the method described in The Journal of Antibiotics, vol. XL, No. 1, page 81] was added to this solution, and the reaction mixture was stirred for 2 hours at room temperature. After reaction, ethyl acetate was added to the reaction mixture and the organic layer was washed with saturated sodium bicarbonate aqueous solution and saline, and dried over magnesium sulfate. The solvent was removed under reduced pressure and the resulting residue was purified by silica gel column chromatography (10% methanol-chloroform) to give 309 mg of (43%) of 1-[(cyclohexyloxy)carbonyloxy] ethyl (1R,5S,6S)-2-[1-(1,3-thiazolin-2-yl)azetidin-3-yl]thio-6-[(R)-1-hydroxyethyl]-1-methylcarbapen-2-em-3-carboxylate [Compound (33)].

$^1$H-NMR (CDCl$_3$) δ: 1.219 (d, 3H, J=7.3 Hz), 1.323 (d, 3H, J=6.3 Hz), 1.37–1.50 (m, 2H), 1.563 (d, 1.5H, J=5.3 Hz), 1.611 (d, 1.5H, J=5.3 Hz), 1.67–1.82 (m, 4H), 1.90–2.05 (m, 4H), 3.20 (m, 1H), 3.216 (dd, 1H, J=2.7 Hz, 6.9 Hz), 3.367 (t, 2H, J=7.6 Hz), 3.92–4.04 (m, 4H), 4.08–4.25 (m, 3H), 4.34–4.43 (m, 2H), 4.59–4.71 (m, 1H), 6.880 (q, 0.5H, J=5.3 Hz), 6.890 (q, 0.5H, J=5.3 Hz)

EXAMPLE 7

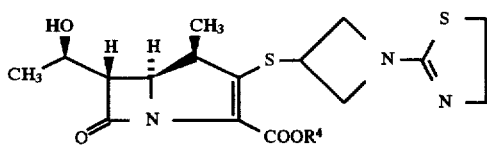

Other ester compounds of (1R,5S,6S)-2-[1-(1,3-thiazolin-2-yl)azetidin-3-yl]thio-6-[(R)-1-hydroxyethyl]-1-methyl-carbapen-2-em-3-carboxylic acid represented by the above formula were obtained by reacting Compound (28) with Compound (18) [obtained in the Preparation 4], Compound (20) [obtained in the Preparation 5] and Compound (24) [obtained in the Preparation 6] respectively.

EXAMPLE 8

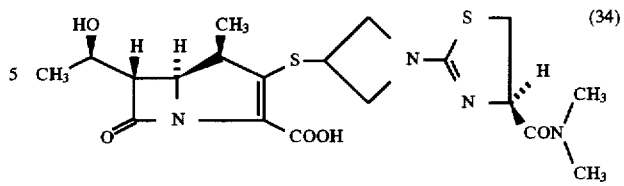

Compound (34) was obtained in substantially the same manner as that of Examples 1 and 2.

$^1$H-NMR (D$_2$O) δ: 1.16 (d, 3H, J=6.9 Hz), 1.27 (d, 3H, J=6.3 Hz), 2.95 (s, 3H), 3.11 (s, 3H), 3.19 (m, 1H), 3.41 (dd, 1H, J=2.5 Hz, 6.1 Hz), 3.57 (dd, 1H, J=5.9 Hz, 11.5 Hz), 3.89 (dd, 1H, J=8.6 Hz, 11.5 Hz), 4.11–4.37 (m, 5H), 4.62–4.80 (m, 2H), 5.37 (dd, 1H, J=5.9 Hz, 8.6 Hz)

The carbapenem compounds according to the present invention may be formulated in various preparation forms.

Formulation Example 1 (Injection)

| (1) Injectable suspension: | |
|---|---|
| Compound (28) | 25.0 g |
| Methy cellulose | 0.5 g |
| Polyvinyl pyrrolidone | 0.05 g |
| Methyl p-oxybenzoate | 0.1 g |
| Polysolvate 80 | 0.1 g |
| Lidocaine hydrochloride | 0.5 g |
| Distilled water | to make 100 ml |

The above components were formulated into 100 ml of an injectable suspension.

(2) Lyophilization

An appropriate amount of distilled water was added to 20 g of the sodium salt of Compound (28) to make a total volume of 100 ml. The above solution (2.5 ml) was filled in vials so as for each vial to contain 500 mg of the sodium salt of Compound (28) and lyophilized. The lyophilized vial was mixed in situ with approximately 3–4 ml of distilled water to make an injectable solution.

(3) Powder

Compound (28) was filled in an amount of 250 ml in a vial and mixed in situ with about 3–4 ml of distilled water to make an injectable solution.

Formulation Example 2 (Tablets)

| Compound (33) | 25 g |
|---|---|
| Lactose | 130 g |
| Crystalline cellulose | 20 g |
| Corn starch | 20 g |
| 3% aqueous solution of hydroxypropyl cellulose | 100 ml |
| Magnesium stearate | 2 g |

Compound (33), lactose, crystalline cellulose, and corn starch were screened through a 60-mesh sieve, homogenized, and charged into a kneader. A 3% aqueous solution of hydroxypropyl cellulose was added and the mixture was kneaded. The product was granulated by a 16-mesh sieve, dried in air at 50° C., and again granulated by a 16-mesh sieve. Magnesium stearate was added to the granule and mixed. The mixture was tabletted to produce tablets weighing 200 mg each and having an 8 mm diameter.

Formulation Example 3 (Capsules)

| Compound (33) | 25 g |
|---|---|
| Lactose | 125 g |
| Corn starch | 48.5 g |
| Magnesium stearate | 1.5 g |

The above components were finely pulverized and thoroughly mixed to produce a homogeneous mixture. The mixture was filled in gelatin capsules, 0.2 g per capsule, to obtain capsules for oral administration.

Formulation Example 4 (Tablets)

| Compound (32) | 25 g |
|---|---|
| Lactose | 130 g |
| Crystalline Cellulose | 20 g |
| Corn starch | 20 g |
| 3% aqueous hydroxypropyl cellulose | 100 ml |
| Magnesium stearate | 2 g |

Compound (32), lactose, crystalline cellulose, and corn starch were screened through a 60-mesh sieve, homogenized, and charged into a kneader. The 3% aqueous solution of hydroxypropyl cellulose was added and the mixture was kneaded. The product was granulated by a 16-mesh sieve, dried in air at 50° C., and again granulated by a 16-mesh sieve. Magnesium stearate was added to the granule and mixed. The mixture was tabletted to produce tablets weighing 200 mg each and having an 8 mm diameter.

Formulation Example 5 (Troche)

| Compound (33) | 200 mg |
|---|---|
| Sugar | 770 mg |
| Hydroxypropyl cellulose | 5 mg |
| Magnesium stearate | 20 mg |
| Flavor | 5 mg |
| | 1,000 mg/troche |

The components were mixed with each other and formulated into troches by punching in conventional manner.

Formulation Example 6 (Capsules)

| Compound (33) | 500 mg |
|---|---|
| Magnesium stearate | 10 mg |
| | 510 mg/capsule |

The components were mixed with each other and filled in conventional hard gelatin capsules.

Formulation Example 7 (Dry Syrup)

| Compound (33) | 200 mg |
|---|---|
| Hydroxypropyl cellulose | 2 mg |
| Sugar | 793 mg |
| Flavor | 5 mg |
| | 1,000 mg |

The above components were mixed with each other and formulated into dry syrups in conventional manner.

Formulation Example 8 (Powders)

| (1) Compound (33) | 200 mg |
|---|---|
| Lactose | 800 mg |
| | 1,000 mg |
| (2) Compound (33) | 250 mg |
| Lactose | 750 mg |
| | 1,000 mg |

The components were mixed with each other and formulated in powders in conventional manner.

Formulation Example 9 (Suppository)

| Formulation Example 9 (Suppository): | |
|---|---|
| Compound (33) | 500 mg |
| Witepsol H-12 | 700 mg |
| (Product of Dynamite Noble) | |
| | 1,200 mg |

The above components were mixed with each other and formulated into suppositories in conventional manner.

SECOND EMBODIMENT OF THE INVENTION

The substituent designation of the formulae according to the second embodiment are specific to the second embodiment and may be the same or different than the substituent designation of formulae of the first embodiment.

The second embodiment of the present invention relates to thiol compounds, and, more detailedly, to novel thiol compounds which are useful as synthesis intermediates for a certain kind of orally administrable carbapenem compound which shows strong antibacterial activity, and to acid addition salts of said thiol compounds, and further to the processes for the production of these compounds, and, moreover, to novel synthesis intermediates which are useful in said production processes.

There have heretofore been found out a lot of compounds having what is called a carbapenem skeleton, and, from among such compounds, there have been proposed some ones having excellent antibacterial activity. On account of their low absorbability from alimentary canal, however, most of the carbapenem compounds which have so far been proposed are clinically though to be administered as injections only.

In view of the purpose of therapy or circumstances on the side of patients, it is desirable in clinical practice that several dosage routes can be selected for the administration of medicines. Compared with injections, oral drugs are especially preferable and clinically quite useful since they can be administered easily and conveniently, and since they can be administered also in one's own home.

Clinically, therefore, there have bene strong demands for the development of carbapenem compounds which have a wide range of antibacterial spectrum and strong antibacterial activity and which can orally be administered.

Under the above-mentioned circumstances, the authors of this invention made studies over and over again about orally administrable carbapenem compounds, and found that compounds which have, as a substituent at the 2-position of carbapenem skeleton, a 1-(1,3-thiazolin-2-yl)azetidin-3-ylthio group represented by the following formula (X)

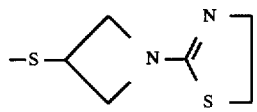

or, typically, such a carbapenem compound as is represented by the following formula (IX)

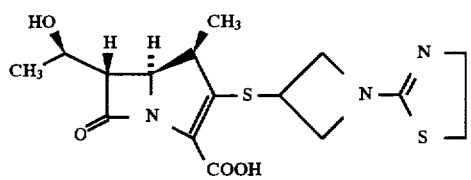

exhibits per se high antibacterial activity, and that, moreover, an ester derivative which is prepared by esterifying the carboxyl group at 3-position of the above compound with a specific ester residue has excellent absorbability from alimentary canal and, besides, is converted again to the compound of the above formula (IX) when rapidly hydrolyzed in vivo, and thus found that, therefore, the above-mentioned ester derivative can be used as a clinically excellent antibacterial agent, especially, for oral administration, in the form of a prodrug of the compound of the above formula (IX), and, thus, they have already applied for a patent with regard to the compound of the above formula (IX) and their ester derivatives (Japanese Patent Application No. 6-170496; U.S. patent application Ser. No. 8/267397; EP-A-632039 etc.).

The main object of the present invention is to provide a synthesis intermediate for the purpose of efficiently introducing a 1-(1,3-thiazolin-2-yl)azetidin-3-ylthio group represented by the above formula (X), which is a characteristic substituent at the 2-position of the compounds of the above formula (IX), into a carbapenem skeleton.

The other objects of this invention will be seen clearly from the following description:

This invention provides 3-mercapto-1-(1,3-thiazolin-2-yl)azetidine which is represented by the following formula (I) and its acid addition salts:

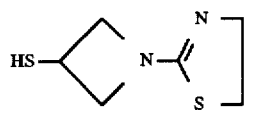

The compound which is represented by the above formula (I) and its acid addition salts are quite useful as key intermediates for the industrial-scale efficient production of the clinically quite useful carbapenem compound represented by the above formula (IX) which exhibits per se high antibacterial activity, and which becomes orally administrable when esterified.

Examples of the acid addition salts of the compound of the above formula (I) include addition salts with organic acids like lower aliphatic acids such as acetic acid, propionic acid, butyric acid, trifluoroacetic acid and trichloroacetic acid; substituted or unsubstituted benzoic acids such as benzoic acid and p-nitrobenzoic acid; (halo)lower alkylsulfonic acids such as methanesulfonic acid and trifluoromethanesulfonic acid; substituted or unsubstituted aryl sulfonic acids such as benzenesulfonic acid, p-nitrobenzenesulfonic acid, p-bromobenzenesulfonic acid, toluenesulfonic acid and 2,4,6-triisopropylbenzenesulfonic acid; and organic phosphoric acids such as diphenylphosphoric acid; as well as addition salts with inorganic acids like hydrochloric acid, sulfuric acid, hydrobromic acid, hydroiodic acid, fluoroboric acid, perchloric acid and nitrous acid.

The compound of the above formula (I) can be efficiently produced by any of the following three characteristic processes A, B and C, for example:

Process variant A

In this process, the compound of the above formula (I) is produced from 2-halomethyl aziridine as a starting material by the path shown in the following reaction scheme (A):

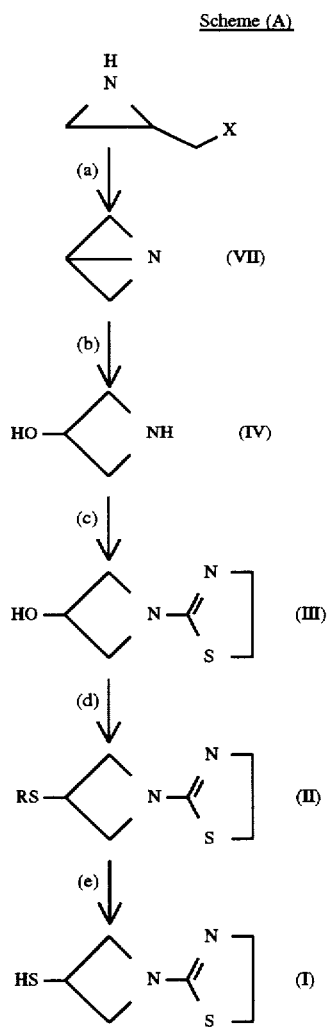

In the above formulae, R denotes an acyl group, a substituted or unsubstituted lower alkyl group or an aryl group; and X denotes a halogen atom.

In this specification, the term "lower" means that the number of the carbon atoms to which this term is attached is six or less, preferably four or less.

"Lower alkyl group" may be either straight-chain one or branched-chain one. Examples thereof include methyl, ethyl, n-propyl, isopropyl, n-butyl, isobutyl, sec-butyl, tert-butyl, n-pentyl, isopentyl, n-hexyl, isohexyl, n-heptyl and isoheptyl. Preferable among them are methyl, ethyl, n-propyl, isopropyl n-butyl, isobutyl, sec-butyl and tert-butyl. Under circumstances, these lower alkyl groups may be substituted with a phenyl group which may further be substituted with at least one, preferably one or two, substituent which is selected from the group consisting of hydroxy, methoxy, acetoxy and nitro.

"Acyl group" may be such one as is left after hydroxyl group is removed from the carboxyl portion of organic carboxylic acids. Examples of acyl groups include lower alkanoyl groups such as acetyl, propionyl and butyryl, or a substituted or unsubstituted benzoyl group.

"Aryl group" may be monocyclic or polycyclic, and, further, may have one or more substituent such as lower alkyl group, nitro group and halogen atom on its ring. Examples of aryl group include phenyl, tolyl, xylyl, α-naphtyl and β-naphtyl groups.

"Halogen atom" includes fluorine, chlorine, bromine and iodine atoms, and, among these, chlorine, bromine and iodine atoms are preferable.

In the following, the method shown by Scheme (A) is minutely explained in accordance with each step:

Step (a)

In this step, 2-halomethyl aziridine is made to react with a base, and, thus, is converted into 1-azabycyclo[1.1.0]butane which is represented by formula (VII).

The above reaction is conducted as follows: 2-halomethyl aziridine is dissolved or suspended in a reactionally inert solvent selected from among alcohol type solvent such as methanol, ethanol, propanol and n-butanol; ether type solvent such as diethyl ether and tetrahydrofuran; hydrocarbon type solvent such as n-heptane, n-hexane, cyclohexane, pentane and cyclopentane; ester type solvent such as methyl acetate ester and ethyl acetate ester; halogen type solvent such as dichloromethane, chloroform and carbontetrachloride; or acetonitrile, dimethylformamide, dimethylacetamide, dimethylsulfoxide and the like; preferably, ether type solvent such as diethyl ether and tetrahydrofuran, and, to the resultant solution or suspension, there are added suitable bases selected from organic and inorganic bases like alkaline metals such as lithium, sodium and potassium; alkaline earth metals such as calcium and magnesium; alkaline metal hydrides such as lithium hydride and sodium hydride; alkaline earth metal hydrides such as calcium hydride; alkaline metal hydroxides such as sodium hydroxide and potassium hydroxide; alkaline metal carbonates such as sodium carbonate and potassium carbonate; alkaline metal hydrogencarbonates such as sodium hydrogencarbonate and potassium hydrogencarbonate; alkaline metal alkyls such as methyllithium and n-butyllithium; alkyl Grignard reagents; alkaline metal amides such as lithiumamide, lithiumdiisopropylamide, sodiumamide and potassiumamide; alkaline metal alkoxides such as sodiummethoxide, sodiumethoxide and potassium tertiary butoxide; alkaline metal alkanoates such as sodium acetate; alkaline earth metal carbonates such as magnesium carbonate and calcium carbonate; tri(lower)alkylamine such as trimethylamine, triethylamine, N,N-diisopropyl-N-ethylamine; pyridine compounds such as pyridine, picoline, lutidine, N,N-di(lower)alkylaminopyridine like N,N-dimethylaminopyridine; quinolines; N-(lower)alkylmorpholine such as N-methylmorpholine; N,N-di(lower)alkylbenzylamine such as N,N-dimethylbenzylamine; and DMSO salts which are made from DMSO and sodium hydride or lithium hydride: preferably, alkyl lithium such as methyl lithium and n-butyllithium, and alkaline metal amides such as lithium amide and lithium diisopropylamide, and, then, the resultant mixture is stirred.

The amount of the above bases used in this reaction is not especially restricted. Usually, the bases are used at the proportion of about 1 to about 20 moles, preferably about 1.5 to about 5 moles, per mole of 2-halomethylaziridine. The reaction temperature is not strictly limited, and may be adequately changed according to the species and amount of the bases used. Usually, the reaction is suitably carried out at the temperature in the range of about −78° C. to about 100° C. preferably about −78° C. to about 60° C., and, under such conditions, the reaction can be completed in about 10 minutes to several days.

The reaction is preferably conducted in the stream of inert gas such as nitrogen or argon gas.

The above-mentioned step gives the compound of formula (VII) with a good yield, and the reaction liquid can be employed as it is for the subsequent step. If necessary, by means of subjecting the reaction liquid to a conventional purification measure such as distillation, extraction, washing, solvent evaporation, and column or thin-layer chromatography, the compound of formula (VII) can be isolated and purified.

Examples of 2-halomethylaziridine as a synthesis material used in the above reaction include 2-chloromethylaziridine, 2-bromomethylaziridine and 2-iodomethylaziridine. These compounds can be easily synthesized from allylamine on the market in accordance with the method mentioned in the following Examples 1 or 2.

Step (b)

In this step, 1-azabicyclo[1.1.0]butane of formula (VII) obtained in the above step (a) is made to react with a carboxylic acid, and the resultant compound is subjected to solvolysis, and, thus, is converted into 3-hydroxyazetidine of formula (IV).

In this reaction, the compound of formula (VII) is firstly dissolved in a reactionally inert solvent like ether type solvent such as diethyl ether and tetrahydrofuran which are mentioned in the above step (a), and, then, a carboxylic acid is added to the resultant solution, and the mixture is stirred.

The aforementioned carboxylic acid may be appropriately selected from among formic acid and the organic acids which are mentioned above as forming acid addition salts of the compound of formula (I). Especially preferable are formic acid and acetic acid.

The amount of the carboxylic acid used in this reaction is not especially restricted. Usually, the carboxylic acid is used at the proportion of about 1 to about 20 moles, preferably about 1.5 to about 5 moles, per mole of the compound of formula (VII). The reaction temperature is not strictly limited, and may be adequately changed according to the species and amount of the carboxylic acid used. Usually, the reaction is suitably carried out at a temperature in the range of about −78° C. to about 100° C., preferably about −78° C. to about 60° C., and, under such conditions, the reaction can be completed in about 10 minutes to several days.

The reaction is preferably conducted in the stream of inert gas such as nitrogen or argon gas.

Next, the compound obtained by the above reaction is subjected to solvolysis such as hydrolysis, and, thus, there can be produced 3-hydroxyazetidine of formula (IV).

Said solvolysis reaction is conducted by treating the compound obtained from the above reaction either in water or in alcohol type solvent such as methanol, ethanol and isopropanol or in a mixed solvent composed of water and organic solvent such as acetonitrile, tetrahydrofuran and dioxane, and in the presence of suitable base or inorganic acid such as hydrochloric acid, sulfuric acid, hydrobromic acid and hydroiodic acid which are mentioned in the above step (a), at a temperature in the range of about −20° C. to about 50° C. preferably at a comparatively as low as about 0° C. to a room temperature, for about 10 minutes to several hours.

If necessary, the reaction liquid obtained by the above step may be subjected to a conventional purification measure such as extraction, washing, solvent evaporation, column or thin-layer chromatography or recrystallization, and then the desired compound of formula (IV) can be isolated and purified. However, without such isolation step, the reaction liquid can be employed as it is for the subsequent step.

Step (c)

In this step, 3-hydroxyazetidine of formula (IV) obtained in the above step (b) is converted into 3-hydroxy-1-(1,3-thiazol in-2-yl)azetidine of formula (III).

This step can be conducted by either the method (i) or (ii) as follows:

(i) The above conversion is carried out by stirring 3-hydroxyazetidine of formula (IV) together with a 2-substituted thiazoline derivative represented by the following formula (V)

wherein L denotes a leaving group in the above-mentioned reactionally inert solvent, preferably alcohol type solvent such as methanol or ethanol, and, preferably, in the presence of the above-mentioned suitable base such as sodium hydrogencarbonate, potassium hydrogencarbonate, sodium carbonate or potassium carbonate.

Examples of the leaving group denoted by the mark L in the compounds of the above formula (V) include azido group; halogen atoms such as chlorine, bromine and fluorine; lower alkanoyloxy groups such as acetoxy and propionyloxy; sulfonyloxy groups such as benzenesulfonyloxy, tosyloxy and methanesulfonyloxy; lower alkoxy groups such as methoxy and ethoxy; and lower alkylthio groups such as methylthio and ethylthio. Especially preferable among these are lower alkylthio groups.

The amount of the base and the compound of formula (V) used in this react on is not especially restricted. Usually, the base and the compound of formula (V) are each used at the proportion of about 1 to about 3 moles, preferably about 1 to about 1.5 mole, per mole of the compound of formula (IV). The reaction temperature is not strictly limited, and may be adequately changed according to the species and amount of the solvent, the base and the compound of formula (V) used. Usually, however, the reaction is suitably carried out at a temperature in the range of a room temperature to about 100° C., preferably a room temperature to about 80° C., and, under such conditions, the reaction can be completed in about 1 to about 24 hours.

The reaction is preferably conducted in the stream of inert gas such as nitrogen or argon gas.

(ii) The conversion from the compound of formula (IV) into the compound of formula (III) can also be carried out by stirring the compound of formula (IV) together with haloethylisothiocyanate in the above-mentioned suitable solvent, preferably in acetonitrile, and, preferably, in the presence of the above-mentioned organic base such as triethylamine.

Examples of the haloethylisothiocyanate used here as a raw material include chloroethylisothiocyanate, bromoethylisothiocyanate and iodoethylisothiocyanate.

The amount of the base and the haloethylisothiocyanate used in this reaction is not especially restricted. Usually, however, the base and the haloethylisothiocyanate are each used at the proportion of about 1 to about 3 moles, preferably about 1 to about 1.5 mole, per mole of the compound of formula (IV). The reaction temperature is not strictly limited, and may be adequately changed according to the species and amount of the base and haloethylisothiocyanate. Usually, however, the reaction is suitably carried out at a temperature in the range of about −20° C. to about 50° C. preferably comparatively as low as about 0° C. to a room temperature, and, under such conditions, the reaction can be completed in about 10 minutes to several hours.

The reaction is preferably conducted in the stream of inert gas such as nitrogen or argon gas.

Whichever method (i) or (ii) is carried out, the reaction liquid may be subjected to a conventional purification measure such as extraction, washing, solvent evaporation, column or thin-layer chromatography or recrystallization if need be, and then the compound of formula (III) can be isolated and purified. Moreover, also when stirred together with the organic and inorganic acids which are mentioned above as forming acid addition salts of the compound of formula (I) in a suitable solvent, the compound of formula (III) can be isolated as an acid addition salt.

The compound of formula (III) prepared in the above manner is a novel compound which has never been mentioned in any other literatures, and constitutes a part of the present invention.

Step (d)

In this step, 3-hydroxy-1-(1,3-thiazolin-2-yl)azetidine of formula (III) obtained in the above step (c) is converted into 3-mercapto-1-(1,3-thiazolin-2-yl)azetidine derivatives of formula (II).

This step can be conducted by either the method (i) or (ii) as follows:

(i) The above conversion can be carried out by activating the hydroxyl group of the compound of formula (III), and, thereafter, by making the resultant activated derivative react with a compound represented by formula RSH (wherein R is as defined above) or with its salt.

Examples of the thiol compound represented by formula RSH include thioacetic acid, thiopropionic acid, thiobenzoic acid, t-butylmercaptan, benzylmercaptan, benzhydrylmercaptan, tritylmercaptan, benzylmercaptan whose phenyl group is substituted with one or two hydroxy, methoxy, acetoxy or nitro, phenylmercaptan which may be substituted with lower alkyl group, nitro group or halogen atom, or naphthyl mercaptan. Preferable among these are thiol compounds whose R denotes lower alkanoyl group or substituted or unsubstituted benzoyl group. Furthermore, this thiol compound may take the form of a salt with alkaline metal such as sodium and potassium.

The reaction to activate the hydroxyl group of the compound of formula (III) can be conducted by allowing the compound of formula (III) to react with an hydroxyl group-activating reagent like organic sulfonylhalide such as methanesulfonyl chloride and 4-toluenesulfonyl chloride or acylhalide such as acetylchloride in the above-mentioned inert solvent like ether type solvent such as diethylether and tetrahydrofuran, and, preferably, in the presence of the above-mentioned suitable base like organic bases such as triethylamine, diisopropylethylamine and N,N-dimethylaminopyridine, or a combination thereof.

The amount of the base and the hydroxyl group-activating reagent used in this reaction is not especially restricted. Usually, however, the base and the activating reagent are each used at the proportion of about 1 to about 3 moles, preferably about 1 to about 1.5 mole, per mole of the compound of formula (III). The reaction temperature is not strictly limited, and may be adequately changed according to the species and amount of the base and the activating reagent. Usually, however, the reaction is suitably carried out at a temperature in the range of about −20° C. to about 50° C., preferably comparatively as low as about 0° C. to a room temperature, and, under such conditions, the reaction can be completed in about 10 minutes to several hours.

The reaction is preferably conducted in the stream of inert gas such as nitrogen or argon gas.

Then, the compound of formula (III) whose hydroxyl group has been activated is stirred together with the above compound represented by formula RSH or its salt in the above-mentioned suitable solvent such as dimethylformamide, and, thus, there can be obtained the desired compounds of formula (II) intended in this step.

The amount of the thiol compound represented by formula RSH or its salt used in this reaction is not especially restricted. Usually, however, the compound or its salt is used at the proportion of about 1 to about 8 moles, preferably about 1 to about 6 moles, per mole of the compound whose hydroxyl group has been activated. The reaction temperature is not strictly limited, and may be adequately changed according to the species and amount of the thiol compound or its salt. Usually, however, the reaction is suitably carried out at a temperature in the range of about 0° C. to about 150° C., preferably a room temperature to about 120° C., and, under such conditions, the reaction can be completed in about 10 minutes to several hours.

The reaction is preferably conducted in the stream of inert gas such as nitrogen or argon gas.

(ii) The conversion of the compound of formula (III) to the compounds of formula (II) can be also conducted by making the compound of formula (III) react with di(lower)alkylazodicarboxylate, triphenylphosphine and the above compound represented by RSH.

Examples of di(lower)alkylazodicarboxylate used here include diethylazodicarboxylate and diisopropylazodicarboxylate. As for the compound represented by RSH, there can be employed those mentioned in the above (i).

The reaction can be carried out by stirring the compound of formula (III) together with di(lower)alkylazodicarboxylate, triphenylphosphine and the compound represented by RSH in the above-mentioned suitable solvent like ether type solvent such as diethylether and tetrahydrofuran.

The amount of the di(lower)alkylazodicarboxylate, triphenylphosphine and the compound represented by RSH used in this reaction is not especially restricted. Usually, however, these compounds are each used at the proportion of about 1 to about 3 moles, preferably about 1 to about 2 moles, per mole of the compound of formula (III). The reaction temperature is not strictly limited, and may be adequately changed according to the species and amount of the reagent and compounds. Usually, however, the reaction is suitably carried out at a temperature in the range of about −20° C. to about 50° C., preferably about 0° C. to a room temperature, and, under such conditions, the reaction can be completed in about 10 minutes to several hours.

The reaction is preferably conducted in the stream of inert gas such as nitrogen or argon gas.

Whichever method (i) or (ii) is carried out, the reaction liquid may be subjected to a conventional purification measure such as extraction, washing, solvent evaporation, column or thin-layer chromatography or recrystallization if need be, and then the compounds of formula (II) can be isolated and purified. Moreover, also when stirred together with the above-mentioned organic acids or inorganic acids in a suitable solvent, the compounds of formula (II) can be isolated in the form of adequate acid addition salts.

Thus obtained compounds of formula (II) are also novel compounds which have never been mentioned in any other literatures, and constitute a part of the present invention.

Step (e)

In this step, 3-mercapto-1-(1,3-thiazolin-2-yl)azetidine derivatives of formula (II) or its acid addition salts obtained in the above step (d) are converted, by means of cleaving off the group R therefrom, into 3-mercapto-1-(1,3-thiazolin-2-yl)azetidine of formula (I) or its acid addition salts of the present invention.

The group R can be cleaved off from the compounds of formula (II) by means of the above-mentioned solvolysis reaction such as hydrolysis, or by the following hydrogenolysis reaction.

Hydrogenolysis can be conducted by treating the compounds of formula (II) in, for example, a buffer solution of pH 5–7 such as an acetate buffer solution, a morpholinopropanesulfonate-sodium hydroxide buffer solution or a phosphate buffer solution; a mixed solvent composed of these buffer solutions and alcoholic solvent; or in a mixed solvent such as tetrahydrofuran-water, tetrahydrofuran-ethanol-water, dioxane-water, dioxane-ethanol-water and n-butanol-water each containing dipotassium phosphate, sodium bicarbonate, and the like; with use of hydrogen of about 1 to 4 atm, in the presence of a hydrogenation catalyst such as platinum oxide, palladium-activated carbon or palladium hydroxide-activated carbon, at a temperature in the range of about 0° C. to about 50° C., for about 0.25 to about 5 hours.

The above step gives the compound of formula (I) of the present invention with a good yield. The reaction liquid may be subjected to a conventional purification measure such as extraction, washing, solvent evaporation, column or thin-layer chromatography or recrystallization if need be, and then the compound of formula (I) can be isolated and purified.

Process variant 8

In the secondarily proposed process, the compound of formula (I) is produced from the compound of formula (VII), which can be prepared by the above-mentioned manner from 2-halomethylaziridine, by the reaction path shown in the following Scheme (B).

Scheme (B)

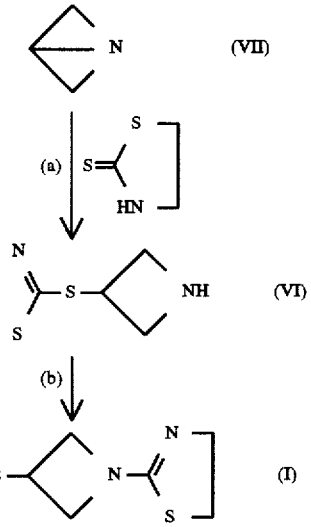

In the following, the method shown in Scheme (B) is minutely explained in accordance with each step:

Step (a)

In this step, 2-(azetidin-3-ylthio)-1,3-hiazoline of formula (VI) is produced by making 1-azabicyclo[1.1.0]butane of formula (VII) react with 1,3-thiazolidine-2-thione.

This reaction can be conducted by stirring 1-azabicyclo[1.1.0]butane of formula (VII) and 1,3-thiazolidine-2-thione in the above-mentioned suitable solvent, preferably in tetrahydrofuran, and preferably in the presence of the above-mentioned suitable base like alkaline metal hydride such as sodium hydride or alkaline metal alkoxide such as sodium methoxide.

The amount of 1,3-thiazolidine-2-thione and the base used in this reaction is not especially restricted. Usually, however, they are each used at the proportion of about 1 to about 3 moles, preferably about 1 to about 1.5 mole, per mole of 1-azabicyclo[1.1.0]butane of formula (VII). The reaction temperature is not strictly limited, and may be adequately changed according to the species and amount of 1,3-thiazolidine-2-thione and the base. Usually, however, the reaction is suitably carried out at a temperature in the range of about −78° C. to about 100° C., preferably −78° C. to a room temperature, and, under such conditions, the reaction can be completed in about 1 hour to about 24 hours.

The reaction is preferably conducted in the stream of inert gas such as nitrogen or argon gas.

The above step gives the compound of formula (VI) with a good yield. The reaction liquid may be subjected to a conventional purification measure such as extraction, washing, solvent evaporation, column or thin-layer chromatography or recrystallization if need be, and then the compound of formula (VI) can be isolated and purified. Moreover, when stirred together with the above organic or inorganic acid in a suitable solvent, the compound of formula (VI) can be isolated as a suitable acid addition salt.

The obtained compound of formula (VI) is a novel compound which has never been mentioned in any other literatures, and constitutes a part of the present invention.

Step (b)

In this step, 2-(azetidin-3-ylthio)-1,3-thiazoline of formula (VI) obtained in the above step (a) is treated with acid, and, thus, is converted into 3-mercapto-1-(1,3-thiazolin-2-yl)azetidine of formula (I) in accordance with the present invention.

This reaction can be carried out by stirring the above compound of formula (VI) and an acid in the above-mentioned suitable solvent, preferably in tetrahydrofuran. Examples of the above mentioned acid include the organic and inorganic acids which are mentioned above as forming acid addition salt of the compound of formula (I). Preferably used among them are lower alkylsulfonic acids such as methylsulfonic acid.

The amount of acid used in this reaction is not especially restricted. Usually, however, it is used at the proportion of about 0.1 to about 3 moles, preferably about 0.1 to about 1 mole, per mole of the compound of formula (VI). The reaction temperature is not strictly limited, and may be adequately changed according to the species and amount of the acid. Usually, however, the reaction is suitably carried out at a temperature in the range of a room temperature to about 100° C., preferably a room temperature to about 80° C., and, under such conditions, the reaction can be completed in about 10 minutes to about several hours.

The reaction is preferably conducted in the stream of inert gas such as nitrogen or argon gas.

The above step gives the compound of formula (I) with a good yield. The reaction liquid may be subjected to a usual purification measure such as extraction, washing, solvent evaporation, column or thin-layer chromatography or recrystallization if need be, and then the compound of formula (I) can be isolated and purified.

Process variant C

In the thirdly proposed process, the compound of formula (I) is produced from the compound of formula (VII), which can be prepared by the above-mentioned manner from 2-halomethylaziridine, by the reaction path shown in the following Scheme (C).

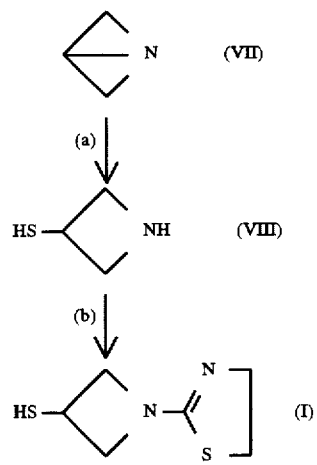

Scheme (C)

In the following, the method shown in Scheme (C) is minutely explained in accordance with each step.

Step (a)

In this step, 1-azabicyclo[1.1.0]butane of formula (VII) is converted into 3-mercaptoazetidine of formula (VIII).

The above reaction can be carried out by stirring the compound of formula (VII) together with the aforementioned compound represented by formula RSH or its salts in such a suitable solvent as mentioned above, and, then, cleaving off the group R from the resultant compound.

Examples of the compound represented by formula RSH or its salts include the above-mentioned compounds. Preferably used among these are compounds whose R denotes a lower alkanoyl group or a substituted or unsubstituted benzoyl group, or salts thereof with sodium and potassium.

The amount of the compound RSH used in this reaction with the compound of formula (VII) is not especially restricted. Usually, however, it is used at the proportion of about 1 to about 5 moles, preferably about 1 to about 3 moles, per mole of the compound of formula (VII). The reaction temperature is not strictly limited, and may be adequately changed according to the species and amount of the compound RSH. Usually, however, the reaction is suitably carried out at a temperature in the range of about −78° C. to about 80° C., preferably −50° C. to a room temperature, and, under such conditions, the reaction can be completed in about 10 minutes to several hours.

The reaction is preferably conducted in the stream of inert gas such as nitrogen or argon gas.

Next, the reaction to cleave off the group R from the compound obtained in the above reaction can be carried out in accordance with the method shown in step (e) of the above process variant A.

Incidentally, when the above reaction is conducted with use of a thiol compound whose R is acyl group as a starting material, there is added a group R in two molar equivalents to the compound of formula (VII) under circumstances (See: Example 9 which is mentioned later). In this case, however, the group R can also be cleaved off in accordance with the method shown in step (e) of the above process variant A (See: Example 10 which is mentioned later).

The above step gives the compound of formula (VIII) with a good yield. The reaction liquid may be subjected to a conventional purification measure such as extraction, washing, solvent evaporation, column or thin-layer chromatography or recrystallization if need be, and then the compound of formula (VIII) can be isolated and purified. Moreover, when stirred together with the above organic or inorganic acid in a suitable solvent, the compound of formula (VIII) can be isolated as a suitable acid addition salt.

Step (b)

In this step, the compound of formula (VIII) obtained in the above step (a) is made to react with the above mentioned 2-substituted-1,3-thiazoline derivatives of formula (V), and, thus, there is produced the compound of formula (I) in accordance with the present invention.

This step can be conducted in the same manner as the method (i) or (ii) of step (c) in the above process variant A.

Whichever method (i) or (ii) is employed, the reaction liquid may be subjected to a conventional purification measure such as extraction, washing, solvent evaporation, column or thin-layer chromatography or recrystallization if need be, and then the compound of formula (I) can be isolated and purified.

When stirred together with the above organic or inorganic acid in a suitable solvent, the compound of formula (I) which is obtained by the above process variants A to C can be isolated in the form of acid addition salts. Among thus obtained acid addition salts, the salt with inorganic acid, especially hydrochloric acid, can easily be obtained in the form of crystal having excellent storage stability as shown in Examples stated below, and is quite useful as a synthesis intermediate for long-period storage.

In the above stated manner, there can be produced 3-mercapto-1-(1,3-thiazolin-2-yl)azetidine of formula (I) or its acid addition salts which is intended in the present invention.

As stated concretely in Example 13 mentioned below, when Scheme (D) mentioned below is followed with use of the compound of formula (I) which is provided by the present invention, there can be obtained, with good yield, the carbapenem compound of formula (IX) which has excellent antibacterial activity and which becomes orally administrable when esterified.

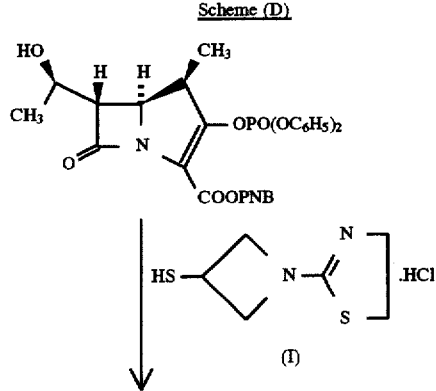

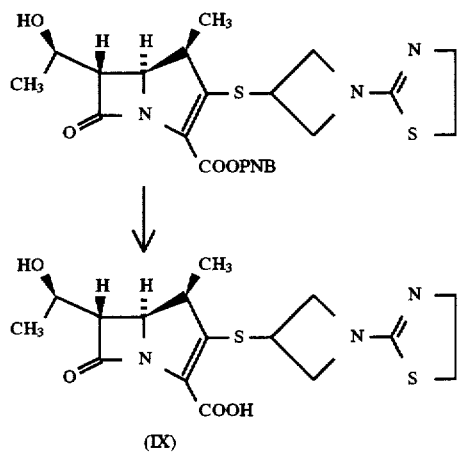

In the following, this invention is more detailedly explained by Examples, Production Examples and Experimental Examples. This invention is, however, not restricted at all by the following descriptions.

Incidentally, the marks in the descriptions have the following meanings:

Ac: acetyl
PNB: p-nitrobenzyl

Example 1

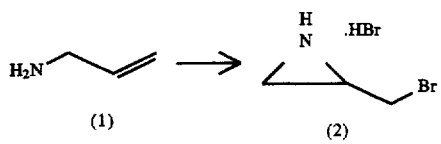

In 94 ml of bromine solution dissolved in 110 ml of diethylether, there was added 80 g of allylamine (1) dropwise at a temperature of 15° C. or less, and was stirred for a day at a room temperature. After the reaction was over, the crystal which had deposited was taken out by filtration, and was washed with 55 ml of diethyl ether, and, then, was subjected to vacuum drying, and, thus, there was obtained 302.6 g (yield: 99.6%) of 2-bromomethylaziridine hydrobromide (2).

H-NMR (CD$_3$OD) δ: 3.35 (dd, 1H, J=9.89 Hz, 14.19 Hz), 3.71 (dd, 1H, J=3.30 Hz, 14.19 Hz), 3.86 (dd, 1H, J=8.58 Hz, 10.89 Hz), 4.01 (dd, 1H, J=4.62 Hz, 10.89 Hz), 4.4–4.6 (m, 1H)

Example 2

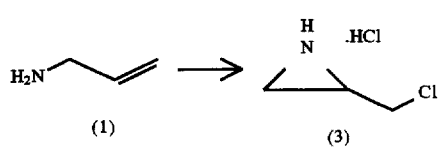

A 900 ml dried solution of dichloromethane containing 9.64 ml of sulfuryl chloride and a catalytic amount of iodine dissolved therein was subjected to reflux at 40° C., and, to this solution, there was added dropwise a 100 ml dried solution of dichloromethane containing 7.6 ml of allylamine (1) dissolved therein, and, after the addition was over, the solution was stirred at the same temperature for two hours. After the reaction was over, the reaction liquid was left still until it had a room temperature, and, then, a residue which was obtained by filtration was washed with dichloromethane and n-hexane, and, next, was subjected to vacuum drying, and, thus, there was obtained 8.37 g (yield: 65.8%) of 2-chloromethylaziridine hydrochloride (3).

$^1$H-NMR (D$_2$O) δ: 3.26 (dd, 1H, J=9.57 Hz, 13.85 Hz), 3.53 (dd, 1H, J=3.30 Hz, 13.85 Hz), 3.78 (dd, 1H, J=6.60 Hz, 12.21 Hz), 3.88 (dd, 1H, J=4.95 Hz, 12.21 Hz), 4.38–4.47 (m, 1H)

Example 3

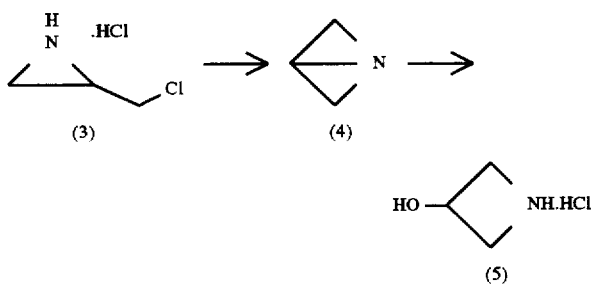

A 25 ml suspension of tetrahydrofuran containing 1.28 g of 2-chloromethylaziridine hydrochloride (3) obtained in the above Example 2 was stirred in the atmosphere of nitrogen at −78° C., and, to this solution, 21 mmol of n-butyllithium was added dropwise over a period of five minutes. After the addition was over, the solution was stirred at the same temperature for one hour, and, while left still so that it might have a room temperature, the solution was further stirred for 10 minutes. To the reaction liquid, there was added 2 ml of 50% aqueous solution of potassium hydroxide, and was stirred for 10 minutes. Thereafter, the reaction liquid was distilled under normal pressure, and, thus, there was obtained 1-azabicyclo[1.1.0]butane (4) having a boiling point of about 51° C. The obtained distillate was dried with potassium hydroxide and potassium carbonate, and, then, was cooled to −40° C., and, to the distillate, there was added dropwise a solution of 5 ml tetrahydrofuran containing 1.13 ml of formic acid. The resultant solution was left still until it had a room temperature, and, then, was further stirred for 18 hours, and, next, the solvent was condensed under reduced pressure, and, to this solution, there was added 16 μl methanol solution containing 60 mmol of concentrated hydrochloric acid at 0° C., and, subsequently, the solution was stirred for 20 hours. After the reaction was over, the solvent was evaporated in a vacuum, and, thus, there was obtained 570 mg (yield: 52.0%) of 3-hydroxyazetidine hydrochloride (5) in the form of colorless needle crystal.

$^1$H-NMR (D$_2$O) δ: 4.0–4.3 (m, 2H), 4.1–4.3 (m, 2H), 4.6–4.8 (m, 1H)

Example 4

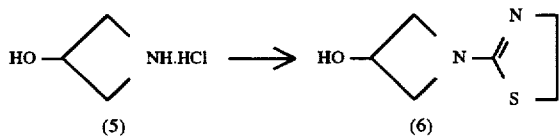

(i) To a 73 ml solution of methanol anhydride containing 7.95 g of 3-hydroxyazetidine hydrochloride (5) obtained in the above Example 3, there was added 5.09 g of potassium hydrogencarbonate at a room temperature, and, then, there was added 9.67 g of 2-(methylthio)-1,3-thiazoline dropwise, and, then, the resultant solution was subjected to heating and reflux for 20 hours. After the reaction liquid was left still until it had a room temperature, 3.63 g of potassium hydrogencarbonate was further added, and the liquid was stirred for one hour at the same temperature. After the reaction was over, precipitate was removed by filtration, and the solvent was evaporated in a vacuum, and, to the obtained residue, there was added 100 ml of tetrahydrofuran, and the resulting mixture was stirred for one hour at a room temperature. Insoluble matters were removed by filtration, and the solvent was evaporated in a vacuum, and, then, the residue was subjected to silica gel column chromatography (eluent: chloroform-methanol), and, thus, there was obtained 8.23 g (yield: 71.5%) of 3-hydroxy-1-(1,3-thiazolin-2-yl)azetidine (6) in the form of colorless crystal.

$^1$H-NMR (CDCl$_3$) δ: 3.356 (t, 2H, J=7.26 Hz), 3.70–4.00 (m, 4H), 4.211 (t, 2H, J=8.21 Hz), 4.622–4.705 (m, 1H), 4.971 (s, 1H)

(ii) A 1.5 ml solution of acetonitrile anhydride containing 219 mg of 3-hydroxyazetidine hydrochloride (5) was cooled to 0° C. in the stream of nitrogen, and, to this solution, there were added 0.31 ml of triethylamine and subsequently a 0.3 ml solution of acetonitrile anhydride containing 250 mg of chloroethylisothiocyanate dissolved therein, and the resultant solution was stirred for 30 minutes at the same temperature, and, after left still until it had a room temperature, the solution was further stirred for two hours. Next, dichloromethane was added to the reaction liquid, and the resultant solution was washed with a saturated aqueous solution of potassium carbonate, and, thereafter, the dichloromethane layer was dried with magnesium sulfate, and then was condensed under reduced pressure, and, thus, there was obtained 300 mg (yield: 95%) of 3-hydroxy-1-(1,3-thiazolin-2-yl)azetidine (6) in the form of colorless needle crystal.

The NMR spectrum of this product was utterly identical with that of the product obtained in the above (i).

Example 5

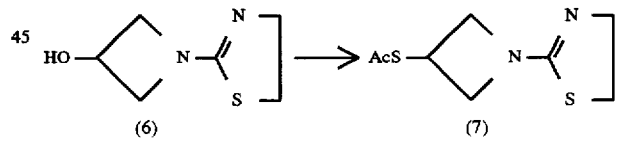

(i) To 2 ml suspension of tetrahydrofuran anhydride containing 790 mg of 3-hydroxy-1-(1,3-thiazolin-2-yl) azetidine (6) obtained in the above Example 4, there was added 6 mg of N,N-dimethylaminopyridine while the suspension was cooled with ice, and, subsequently, there were added dropwise 557 mg of triethylamine and 575 mg of mesyl chloride while the suspension was cooled with ice, and the resulting mixture was stirred for 40 minutes at the same temperature. After the reaction was over, the solvent was evaporated in a vacuum, and, to the resultant residue, there was added ethyl acetate, and the resultant mixture was washed with a saturated aqueous solution of sodium hydrogencarbonate. Then, the resultant aqueous layer was further extracted with ethyl acetate. After the obtained organic layer was dried with magnesium sulfate, the solvent was evaporated in a vacuum, and the residue was subjected to silica gel column chromatography (eluent: chloroform-methanol), and, thus, there was obtained 995 mg (yield: 84.3%) of 3-mesyloxy-1-(1,3-thiazolin-2-yl)azetidine in the form of colorless crystal.

$^{1}$H-NMR (CDCl$_3$, 270 MHz, ppm) δ: 3.07 (s, 3H), 3.39 (t, 2H, J=7.6 Hz), 4.03 (t, 2H, J=7.6 Hz), 4.14–4.19 (m, 2H), 4.37–4.31 (m, 2H), 5.28–5.33 (m, 1H)

Next, to a 1 ml solution of dimethylformamide anhydride containing 118 mg of 3-mesyloxy-1-(1,3-thiazolin-2-yl) azetidine obtained from the above reaction, there was added 228 mg of potassium thioacetate at a room temperature, and the mixture was stirred at 80° C. for four hours. After the reaction was over, the solvent was evaporated in a vacuum, and, then, after ethyl acetate was added, the solution was washed with a saturated aqueous solution of potassium hydrogencarbonate, and, then, the aqueous layer was subjected to back extraction with ethyl acetate. The obtained organic layer was dried with magnesium sulfate, and the residue was subjected to silica gel column chromatography (eluent: chloroform), and, thus, there was obtained 88 mg (yield: 81.2%) of 3-acetylthio-1-(1,3-thiazolin-2-yl)-azetidine (7) in the form of light-yellowish oily matter.

$^{1}$H-NMR (CDCl$_3$) δ: 2.333 (s, 3H), 3.352 (t, 2H, J=7.26 Hz), 3.885 (dd, 2H, J=8.24, 5.28 Hz), 4.012 (t, 2H, J=7.26 Hz), 4.250–4.374 (m, 1H), 4.426 (t, 2H, J=8.25 Hz)

(ii) There were added 119 mg of 3-hydroxy-1-(1,3-thiazolin-2-yl)azetidine (6) and two molar equivalents of thioacetic acid, while cooled with ice, to 10 ml of tetrahydrofuran solution containing two molar equivalents of triphenylphosphine and two molar equivalents of diethylazodicarboxylate, and the resultant solution was stirred for one hour at the same temperature, and for further one hour at a room temperature. The solvent of the reaction liquid was evaporated in a vacuum, and the obtained residue was subjected to silica gel column chromatography (eluent: chloroform-ethanol), and, thus, there was obtained 107 mg (yield: 65%) of 3-acetylthio-1-(1,3-thiazolin-2-yl)azetidine (7).

The NMR spectrum of this product was utterly identical with that of the product obtained in the above (i).

Example 6

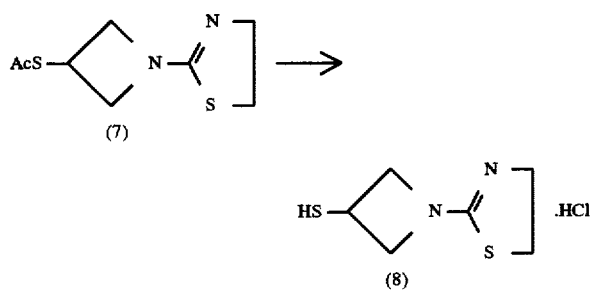

There was dissolved 12.98 g of 3-acetylthio-1-(1,3-thiazolin-2-yl )azetidine (7) obtained in the above Example 5 into 58.3 ml of isopropylalcohol, and to the resultant solution which was being cooled with ice, there was added 37.3 ml solution (1.69N) of potassium hydroxide dissolved in methanol, and the resultant solution was stirred for 10 minutes. Then, at the same temperature, 66 ml solution (2N) of hydrochloric acid in methanol was added to the above solution so that it might be quenched, and, after the resultant mixture was stirred for 15 minutes at a room temperature, insoluble matters were removed by filtration. The residue obtained by condensing the filtrate was dissolved in 39 ml of isopropylalcohol, and, after insoluble matters were removed by filtration, the filtrate was condensed. To the obtained residue, there was added 58.5 ml of n-butanol so that the residue might be condensed, and, thus, there was obtained 3-mercapto-1-(1,3-thiazolin-2-yl)azetidine hydrochloride (8) in the form of yellowish white solid.

To this solid, there was added 22.8 ml of acetonitrile, and the resulting mixture was stirred at a room temperature for 15 minutes so that the mixture might be dissolved, and, then, 113.4 ml of acetone was added dropwise over a period of 30 minutes. Then, further 113.4 ml of acetone was added dropwise over a period of 15 minutes, and, then, the resultant solution was stirred for 30 minutes while cooled with ice. The solid which was deposited was taken by filtration, and then was washed with 150 ml of acetone, and next was dried for a day under reduced pressure, and, thus, there was obtained 10.419 (purity: 97.5%; yield: 80.3%) of 3-mercapto-1-(1,3-thiazolin-2-yl)azetidine hydrochloride (8) in the form of colorless needle crystal.

$^{1}$H-NMR (CDCl$_3$) δ: 2.57 (d, 1H, J=8.2 Hz), 3.59 (t, 2H, J=7.4Hz), 4.02–4.18 (m, 4H), 4.63 (t, 2H, J=7.4 Hz), 5.19–5.26 (m, 1H), 12.19 (s, 1H)

This product was confirmed as a crystal by means of polarizing-microscopic observation. Besides, in powder X-ray diffraction pattern, there was shown a characteristic Peak at each of the following lattice spacing (d) (unit: A)

7.32, 5.96, 5.04, 5.00, 4.90, 4.44, 4.23, 4.08, 3.79, 3.71, 3.66, 3.29, 3.14, 3.10, 2.98, 2.91, 2.82, 2.55, 2.50

Incidentally, both the above crystal filtrate and the acetone washings were condensed, and the resulting residue was dissolved in 10 ml of n-butanol and then was re-condensed, and, next, was dried under reduced pressure for one day. To the obtained 1.7 g of orange solid, there was added 1.7 ml of acetonitrile, and the resulting mixture was stirred for 15 minutes at a room temperature so that it might be dissolved, and, to the resulting solution, there was added 17 ml of acetone dropwise over a period of 15 minutes, and the solution was stirred for 30 minutes while cooled with ice, and, thus, there was obtained 1.2 g (purity: 89.3%; yield: 8.5%) of 3-mercapto-1-(1,3-thiazolin-2-yl)azetidine hydrochloride (8) in the form of colorless needle crystal.

Example 7

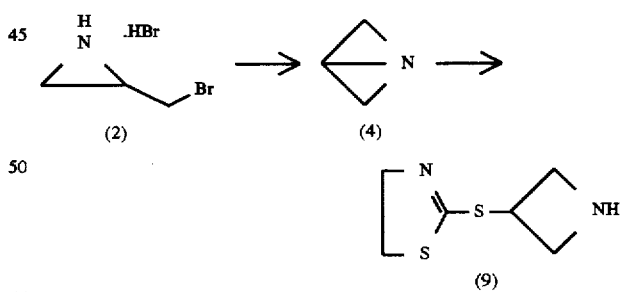

To a 12 ml suspension of dried tetrahydrofuran containing 1.009 of 2-bromomethylaziridine hydrobromide (2) obtained in the above Example 1, there was added dropwise 5.94 ml (1.63M) of of n-butyllithium at −78° C., and the resulting mixture was stirred for one hour. The reaction liquid was distilled under normal pressure in a water bath (90° C.), and each of the evaporated fraction was taken out, and, thus, there was obtained a solution of 1-azabicyclo [1.1.0]butane (4) dissolved in tetrahydrofuran.

To a 5 ml solution of dried tetrahydrofuran containing 550 mg (4.61 mmol) of 1,3-thiazoline-2-thione which was being cooled with ice, on the other hand, there was added 181 mg (55%) of sodium hydride, and the resulting mixture was stirred for one hour. To the obtained solution, there was added dropwise the above solution of 1-azabicyclo[1.1.0] butane dissolved in tetrahydrofuran at −78° C., and the resulting solution was stirred at a room temperature for 20 hours, and, then, the reaction liquid was subjected to high performance liquid chromatography, and, thus, there was obtained 2-(azetidin-3-ylthio)-1,3-thiazolidine (9).

¹H-NMR (CO₃OD) δ: 3.32 (t, 2H, J=8 Hz), 3.46 (dd, 2H, J=6 Hz, 10 Hz), 3.90 (dd, 2H, J=8 Hz, 10 Hz), 4.06 (t, 2H, J=8 Hz) 4.3–4.5 (m, 1H)

Example 8

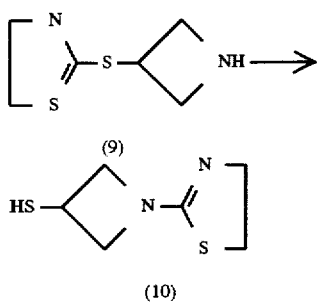

To a solution of tetrahydrofuran anhydride containing 2-(azetidin-3-ylthio)-1,3-thiazolidine (9) obtained in the above Example 7, there was added 0.329 ml of methylsulfonic acid, and, then, the solvent was condensed under reduced pressure, and, to the obtained solution, there was added methanol, and the resulting solution was subjected to heating and reflux for three hours. After the reaction was over, the solvent was distilled off, and the residue was separated and purified by high performance liquid chromatography, and, thus, there was obtained 186 mg (yield: 23.2%) of 3-mercapto-1-(1,3-thiazolin-2-yl)azetidine (10) of the present invention.

The NMR spectrum of the hydrochloride obtained by treating the above compound (10) with hydrochloric acid was utterly identical with that of the compound (8) obtained in the above Example 6.

Example 9

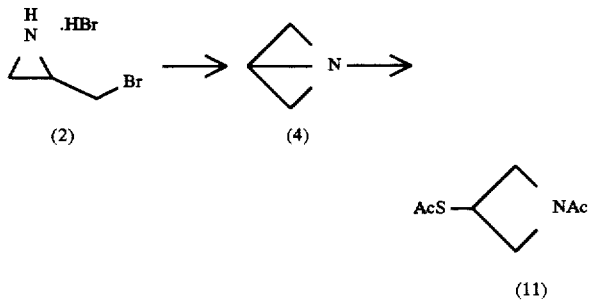

With use of 2.00 g of 2-bromomethylaziridine hydrobromide (2) obtained in the above Example 1, there was produced a solution of 1-azabicyclo[1.1.0]butane (4) dissolved in tetrahydrofuran by the same method as in the above Example 7. Next, to a 5 ml solution of dried tetrahydrofuran containing 1.32 ml of thioacetic acid, there was added dropwise a solution of compound (4) dissolved in tetrahydrofuran at a temperature of −40° C. or lower, and the resulting mixture was stirred at a room temperature for 18 hours. After the reaction was over, the solvent was distilled off, and the residue was separated and purified by silica gel column chromatography (eluent: chloroform-acetone), and, thus, there was obtained 828 mg (yield: 51.8%) of 1-acetyl-3-acetylthioazetidine (11).

¹H-NMR (CDCl₃) δ: 1.87 (s, 3H), 2.35 (s, 3H), 3.89 (dd, ½×2H, J=5 Hz, 10 Hz), 4.01 (dd, ½×2H, J=5 Hz, 9 Hz), 4.1–4.2 (m, 1H), 4.42 (t, ½×2H, J=10 Hz), 4.61 (t, ½×2H, J=10 Hz)

Example 10

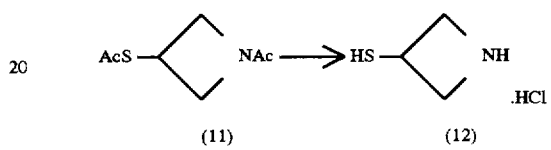

To 104 mg of 1-acetyl-3-acetylthioazetidine (11) obtained in the above Example 9, there was added 1.0 ml of 2.6N hydrochloric acid, and the resulting solution was subjected to heating and reflux for one hour. After the reaction was over, water was added, and the solution was washed with ethylacetate, and, then, the aqueous layer was evaporated in a vacuum. The obtained residue was dried in a vacuum, and, thus, there was obtained 71 mg (yield: 94.4%) of 3-mercaptoazetidine hydrochloride (12).

¹H-NMR (D₂O) δ: 4.0–4.3 (m, 3H), 4.5–4.7 (m, 2H)

Example 11

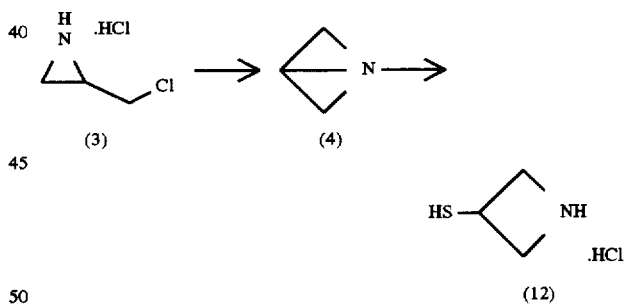

With use of 1.28 g of 2-chloromethylaziridine hydrochloride (3) obtained in the above Example 2, there was produced a solution of tetrahydrofuran containing 1-azabicyclo[1.1.0]butane (4). After this solution was dried with potassium hydroxide and potassium carbonate, there was added dropwise 0.85 ml of thioacetic acid at a room temperature. After the resulting solution was stirred for one hour at the same temperature, the reaction liquid was condensed under reduced pressure, and, then, 3.33 ml of 3 N hydrochloric acid was added, and the resulting solution was subjected to heating and reflux for one hour. After the reaction liquid was left still until it had a room temperature, 30 ml of water was added thereto, and the resulting solution was washed with ethylacetate. The aqueous layer which was obtained by separation was put together with the aqueous layer which had been extracted from organic layer, and, then, the solvent was evaporated in a vacuum, and, thus, there was obtained 913 mg (yield: 72.7%) of 3-mercaptoazetidine hydrochloride (12) in the form of colorless oily matter.

The NMR spectrum of the compound (12) was utterly identical with that of the compound obtained in the above Example 10.

Example 12

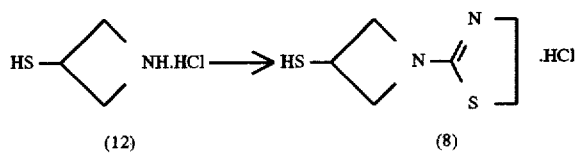

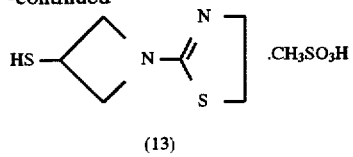

(13)

To a solution of 22.7 mg of 3-mercaptoazetidine hydrochloride (12) obtained in the above Example 11 dissolved in 95% methanol (including 1 ml of water), there were added 26.6 mg of 2-(methylthio)-1,3-thiazoline and 5.2 mg of triphenylphosphine, and the resulting solution was subjected to heating and reflux for six hours. After the reaction was over, the solvent was evaporated in a vacuum, and the obtained residue was dissolved in a 0.1N hydrochloric acid, and the resulting mixture was washed with ethylacetate. The solvent in the obtained aqueous layer was evaporated in a vacuum, and the obtained residue was separated and purified by high performance liquid chromatography, and, thus, there was produced 29.1 mg (yield: 73.4%) of 3-mercapto-1-(1, 3-thiazolin-2-yl)azetidine hydrochloride (8) in the form of colorless needle crystal.

The NMR spectrum of this product was utterly identical with that of the product obtained in the above Example 6.

To a solution of 63.3 mg of 3-mercaptoazetidine hydrochloride (12) obtained in the above Example 10 dissolved in 1.0 ml of dried tetrahydrofuran, there was added 0.07 ml of triethylamine in the stream of nitrogen at a room temperature, and the resulting solution was stirred for 30 minutes. To this solution, there was added dropwise a solution of 70.3 mg of 2-chloroethylisothiocyanate dissolved in dried tetrahydrofuran, and the resulting solution was further stirred for one hour. After the reaction liquid was cooled to 0° C., 0.04 ml of methanesulfonic acid was added dropwise, and the resulting solution was stirred for 30 minutes, and, then, the solvent was evaporated in a vacuum. To the obtained residue, there was added 1.0 ml of dried methanol, and the resulting solution was subjected to heating and reflux for one hour, and, then, the solvent was evaporated in a vacuum. The obtained residue was separated and purified by thin-layer chromatography, and, thus, there was obtained 53.4 mg (yield: 39.2%) of 3-mercapto-1-(1,3-thiazolin-2-yl)azetidine methanesulfonate (13) in the form of colorless oily matter.

Example 14

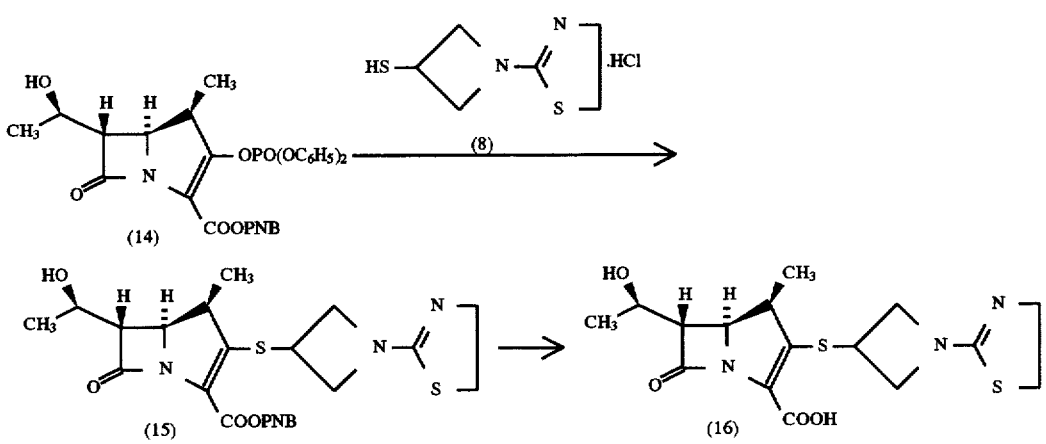

Example 13

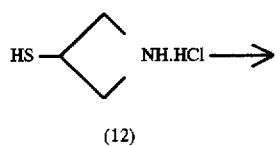

(i) There was dissolved 700 mg of 3-mercapto-1-(1,3-thiazolin-2-yl)azetidine hydrochloride (8), which was obtained in the above Example 6, in 15 ml of a mixed solvent composed of water, acetonitrile and chloroform, and, to the resulting solution, there was added 1668 mg of p-nitrobenzyl (1R, 5R, 6S)-2-(diphenylphosphoryloxy)-6-[(R)-1-hydroxyethyl]-1-methyl-carbapen-2-em-3-carboxylate (14). To the obtained solution which was being cooled with ice, there was added 2.8 ml of diisopropylethylamine in the stream of nitrogen, and the resulting mixture was stirred at the same temperature for two hours. To the reaction liquid, there was added ethylacetate, and the resulting solution was washed with a saturated aqueous solution of sodium hydrogencarbonate and with a saturated aqueous solution of sodium chloride. and, then, the solvent was evaporated in a vacuum, and the obtained residue was subjected to silica gel column chromatography (eluent: chloroform-acetone), and, thus, there was produced 1339 mg (yield: 92%) of p-nitrobenzyl (1R, 5S, 6S)-2-[1-(1,3-thiazolin-2-yl)azetidin-3-yl]thio-6-[(R)-1-hydroxyethyl]-1-methyl-carbapen-2-em-3-carboxylate (15).

$^1$H-NMR (CDCl$_3$) δ: 1.235 (d, 3H, J=7.26 Hz), 1.349 (d, 3H, J=6.27 Hz), 3.160 (quintet, 1H, J=7.26 Hz), 3.265 (dd, 1H, J=2.3, 6.26 Hz), 3.367 (t, 2H, J=7.26 Hz), 3.898~4.038 (m, 4H), 4.071~4.147 (m, 1H), 4.212~4.278 (m, 2H), 4.372 (2H, J=7.92 Hz), 5.255 and 5.517 (d(AB), 2H, J=13.85 Hz), 7.665 (d, 2H, J=8.58 Hz), 8.226 (d, 2H, J=8.58 Hz)

(ii) To a solution of 1339 mg of the compound (15) obtained from the above reaction (i) which was dissolved in 20 ml of tetrahydrofuran, there were added 60 ml of 0.38M phosphate buffer solution (pH 6.0) and 11.2 g of zinc powder, and the mixture was stirred vigorously for two hours. The reaction liquid was filtrated by Celite® so that insoluble matters might be removed, and, then, the filtrate was adjusted to pH 5.5 after washed with ethylacetate. Then, the obtained solution was condensed under reduced pressure, and this condensed solution was subjected to column chromatography Diaion HP-4® (made by Mitsubishi Chemical Corporation) (eluent: 5% aqueous solution of isopropyl-alcohol), and, thus, there was produced 861 mg (yield: 87%) of the desired (1R, 5S, 6S)-2-[1-(1,3-thiazolin-2-yl)azetidin-3-yl]thio-6-[(R)-1-hydroxyethyl]-1-methylcarbapen-2-em-3-carboxylate (16).

$^1$H-NMR (D$_2$O) δ: 1.093 (d, 3H, J=6.93 Hz), 1.207 (d, 3H, J=6.27 Hz), 3.05~3.20 (m, 1H), 3.357 (dd, 1H, J=2.3, 5.94 Hz), 3.558 (t, 2H, J=7.26 Hz), 3.920 (t, 2H, J=7.26 Hz), 4.00~4.20 (m, 5H), 4.20~4.30 (m, 1H), 4.60~4.70 (m, 1H)

IR (KBr): 1740, 1640, 1590 cm$^{-1}$

Experimental Example 1

The 3-mercapto-1-(1,3-thiazolin-2-yl)azetidine hydrochloride (8) in the form of crystal obtained in the above Example 6 was left still in dehumidified state at a room temperature for one month. Resultantly, it was confirmed that the purity of this compound did not change at all, and that it had good storage stability.

Experimental Example 2

There was measured, by the following method, the antibacterial activity of the compound (16) which had been produced in Example 14 with use of the compound (I) of the present invention as a synthesis intermediate.

(1) Test method

There was employed the agar plate dilution method in accordance with the standard method of the Japanese Chemotherapy Society [Chemotherapy, vol. 29, 76–79 (1981)]. Concretely, a Mueller-Hinton (MH) agar liquid medium containing the test microorganism was cultured overnight at 37° C., and the resultant culture medium was diluted with a buffered saline gelatin (BSG) solution so that the concentration of the test microorganism might be about 10 cells/ml. Then, with use of a microplanter, this diluted solution was inoculated each about 5 μl on MH agar media containing the test compounds. Thus, the minimum concentration of the test compound in which no growth of the test microorganism was observed after the incubation at 37° C. for 18 hours was regarded as Minimum Inhibitory Concentration (MIC). Incidentally, all of the test organisms used here were standard strains.

(2) Results

The results of the above experiment are shown in the following Table 1.

TABLE 1

| Test organisms | MIC (μg/ml) Test compound (16) |
|---|---|
| S. aureus FDA209P JC-1 | 0.013 |
| S. aureus Terajima | ≦0.006 |
| S. aureus MS353 | ≦0.006 |
| S. pyogenes Cook | ≦0.006 |
| B. subtilis ATCC 6633 | 0.025 |
| M. luteus ATCC 9341 | 0.2 |
| E. coli NIHJ JC-2 | 0.013 |
| E. coli K-12 C600 | 0.1 |
| E. cloacae 963 | 0.05 |
| E. aerogenes ATCC 13048 | 0.1 |
| K. pneumoniae PCI-602 | 0.013 |
| S. typhimurium IID971 | 0.025 |
| S. typhi 901 | ≦0.006 |
| S. paratyphi 1015 | 0.05 |
| S. schottmuelleri 8006 | 0.025 |
| S. enteritidis G14 | 0.39 |
| S. marcescens IAM 1184 | 0.05 |
| M. morganii IFO 3848 | 0.39 |
| P. mirabilis IFO 3849 | 0.39 |
| P. vulgaris OX-19 | 0.1 |
| P. vulgaris HX-19 | 0.1 |
| P. rettgeri IFO 3850 | 0.39 |

It is known from the above results that the compounds of formula (I) provided by the present invention are useful as intermediates of carbapenem compounds having excellent antibacterial activity.

What we claim is:

1. 3-Mercapto-1-(1,3-thiazolin-2-yl)azetidine represented by formula (I) below and its acid addition salts.

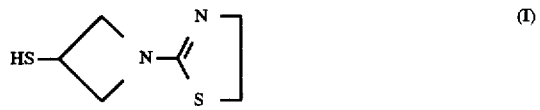

2. The acid addition salts of the compound represented by formula (I) of claim 1, which salts are in the form of crystal.

3. A process to produce the compound represented by formula (I) of claim 1, or its acid addition salts, which process is characterized in that the group R is cleaved off from a 3-mercapto-1-(1,3-thiazolin-2-yl)azetidine derivative represented by formula (II) below or an acid addition salt thereof

wherein R denotes an acyl group, a substituted or un-substituted lower alkyl group or an aryl group.

4. A process to produce the compound represented by formula (I) of claim 1, or its acid addition salts, which process is characterized in that (a) a hydroxyl group-activated derivative of 3-hydroxy-1-(1,3-thiazolin-2-yl)azetidine represented by formula (III) below

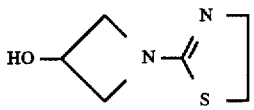 (III)

is made to react with a compound represented by the formula below

RSH wherein R denotes an acyl group, a substituted or un-substituted lower alkyl group or an aryl group or with its salt, and that (b) the group R is cleaved off from the resulting 3-mercapto-1-(1,3-thiazolin-2-yl)azetidine derivative represented by formula (II) below or its acid addition salt

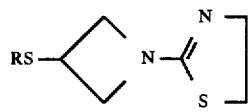 (II)

wherein R is as defined above.

5. A process to produce the compound represented by formula (I) of claim 1, or its acid addition salts, which process is characterized in that (a) 3-hydroxy-1-(1,3-thiazolin-2-yl)azetidine represented by formula (III) below

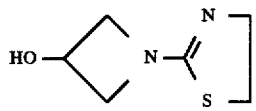 (III)

is made to react with di(lower)alkylazodicarboxylate, triphenylphosphine and a compound represented by the formula below

RSH wherein R denotes an acyl group, a substituted or un-substituted lower alkyl group or an aryl group or its salt, and that (b) the group R is cleaved off from the resulting 3-mercapto-1-(1,3-thiazolin-2-yl)azetidine derivative represented by formula (II) below or its acid addition salt

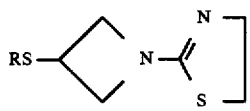 (II)

where in R is as defined above.

6. A process to produce the compound represented by formula (I) of claim 1, or its acid addition salts, which process is characterized in that 2-(azetidin-3-ylthio)thiazoline represented by formula (VI) below

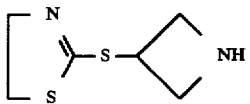 (VI)

is made to react with an acid.

7. A process to produce the compound represented by formula (I) of claim 1, or its acid addition salts, which process is characterized in that 3-mercaptoazetidine represented by formula (VIII) below

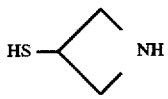 (VIII)

is made to react with a 2-substituted-1,3-thiazoline derivative represented by formula (V) below

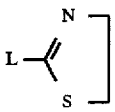 (V)

wherein L denotes a leaving group.

8. A process to produce the compound represented by formula (I) of claim 1, or its acid addition salts, which process is characterized in that 3-mercaptoazetidine represented by formula (VIII) below

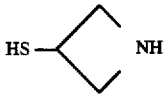 (VIII)

is made to react with haloethylisothiocyanate.

9. A process to produce the compound represented by formula (I) of claim 1, or its acid addition salts, which process is characterized in that (a) after 1-azabicyclo[1.1.0]butane represented by formula (VII) below

 (VII)

is made to react with a compound represented by the formula below

RSH wherein R denotes an acyl group, a substituted or un-substituted lower alkyl group or an aryl group or with its salt, the group R is cleaved off from the resulting compound, and that (b) the obtained 3-mercaptoazetidine represented by formula (VIII) below

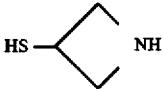 (VIII)

is made to react with a 2-substituted-1,3-thiazoline derivative represented by formula (V) below

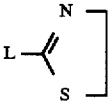 (V)

wherein L denotes a leaving group.

10. A process to produce the compound represented by formula (I) of claim 1, or its acid addition salts, which process is characterized in that (a) after 1-azabicyclo[1.1.0]butane represented by formula (VII) below

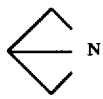
(VII)

is made to react with a compound represented by the formula below

RSH wherein R denotes an acyl group, a substituted or un-substituted lower alkyl group or an aryl group or with its salt, the group R is cleaved off from the resulting compound, and that (b) the obtained 3-mercaptoazetidine represented by formula (VIII) below

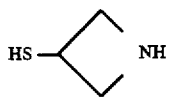
(VIII)

is made to react with haloethylisothiocyanate.

11. 3-Mercapto-1-(1,3-thiazolin-2-yl)azetidine derivatives represented by formula (II) below or acid addition salts thereof

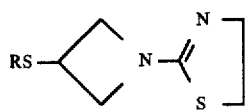
(II)

wherein R denotes an acyl group, a substituted or un-substituted lower alkyl group or an aryl group.

12. A process to produce the compounds represented by formula (II) of claim 11 or acid addition salts thereof, which process is characterized in that a hydroxyl group-activated derivative of 3-hydroxy-1-(1,3-thiazolin-2-yl)azetidine represented by formula (III) below

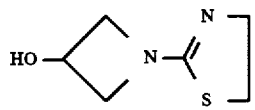
(III)

is made to react with a compound represented by the formula below

RSH wherein R denotes an acyl group, a substituted or un-substituted lower alkyl group or an aryl group or with its salt.

13. 3-Hydroxy-1-(1,3-thiazolin-2-yl)azetidine represented by formula (III) below

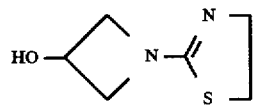
(III)

and its acid addition salts.

14. A process to produce the compound represented by formula (III) of claim 13 or acid addition salts thereof, which process is characterized in that 3-hydroxyazetidine represented by formula (IV) below

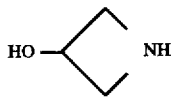
(IV)

is made to react with a 2-substituted-1,3-thiazoline derivative represented by formula (V) below

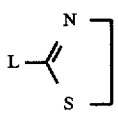
(V)

wherein L denotes a leaving group.

15. A process to produce the compound represented by formula (III) of claim 13 or acid addition salts thereof, which process is characterized in that the compound represented by formula (IV) below

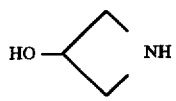
(IV)

is made to react with haloethylisothiocyanate.

16. A process to produce the compound represented by formula (III) of claim 13 or acid addition salts thereof, which process is characterized in that (a) after 1-azabicyclo[1.1.0]butane represented by formula (VII) below

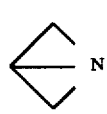
(VII)

is made to react with a carboxylic acid, the resulting compound is subjected to solvolysis, and that (b) the obtained 3-hydroxyazetidine represented by formula (IV) below

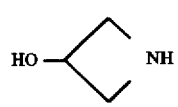
(IV)

is made to react with haloethylisothiocyanate.

* * * * *